US012220805B2

(12) United States Patent
Iida et al.

(10) Patent No.: US 12,220,805 B2
(45) Date of Patent: Feb. 11, 2025

(54) INFORMATION PROCESSING DEVICE AND INFORMATION PROCESSING METHOD

(71) Applicant: SONY GROUP CORPORATION, Tokyo (JP)

(72) Inventors: Fumihiko Iida, Tokyo (JP); Ryuichi Suzuki, Tokyo (JP); Kuniaki Torii, Tokyo (JP); Emika Kaneko, Tokyo (JP)

(73) Assignee: SONY GROUP CORPORATION, Tokyo (JP)

(*) Notice: Subject to any disclaimer, the term of this patent is extended or adjusted under 35 U.S.C. 154(b) by 604 days.

(21) Appl. No.: 17/601,985

(22) PCT Filed: Feb. 14, 2020

(86) PCT No.: PCT/JP2020/005680
§ 371 (c)(1),
(2) Date: May 31, 2022

(87) PCT Pub. No.: WO2020/213245
PCT Pub. Date: Oct. 22, 2020

(65) Prior Publication Data
US 2022/0288791 A1 Sep. 15, 2022

(30) Foreign Application Priority Data

Apr. 16, 2019 (JP) ................. 2019-077700

(51) Int. Cl.
B25J 11/00 (2006.01)
G06F 3/01 (2006.01)

(52) U.S. Cl.
CPC ........... B25J 11/0005 (2013.01); G06F 3/011 (2013.01); G06F 2203/011 (2013.01)

(58) Field of Classification Search
CPC . G06F 2203/011; G06F 3/017; G06F 16/9035
See application file for complete search history.

(56) References Cited

U.S. PATENT DOCUMENTS

| 6,584,439 | B1* | 6/2003 | Geilhufe | G06F 3/167 |
| | | | | 704/E15.045 |
| 10,898,999 | B1* | 1/2021 | Cohen | B25J 9/0003 |
| 2014/0277735 | A1* | 9/2014 | Breazeal | B25J 9/0003 |
| | | | | 700/259 |
| 2017/0365277 | A1* | 12/2017 | Park | G10L 15/1815 |

(Continued)

FOREIGN PATENT DOCUMENTS

| CN | 103106390 A | 5/2013 |
| CN | 107053191 A | 8/2017 |

(Continued)

OTHER PUBLICATIONS

Translations for foreign documents are provided as integrated PDF files provided with this office action.*

(Continued)

Primary Examiner — Jason Holloway
Assistant Examiner — Benjamin J Brosh
(74) Attorney, Agent, or Firm — CHIP LAW GROUP

(57) ABSTRACT

An information processing device including: an output control unit that controls an output from an interaction device to a user; an action evaluation unit that determines an action of the user performed in correspondence with an output of the interaction device; an emotion estimation unit that estimates an emotion of the user corresponding to the action of the user; and an information accumulation unit that accumulates the output of the interaction device, the action of the user, and the emotion of the user in association with each other as interaction information, in which the output control unit controls the output from the interaction device to the user based on the interaction information accumulated.

17 Claims, 16 Drawing Sheets

(56) References Cited

U.S. PATENT DOCUMENTS

| | | | | |
|---|---|---|---|---|
| 2018/0370039 A1* | 12/2018 | Nakagome | ........... | G06V 40/174 |
| 2019/0030723 A1* | 1/2019 | Hayashi | ................. | B25J 11/001 |
| 2019/0337157 A1* | 11/2019 | Sun | ........................ | G10L 25/63 |
| 2020/0114521 A1* | 4/2020 | Mahoor | ................. | B25J 9/1697 |
| 2020/0298414 A1* | 9/2020 | Ogawa | ................. | B25J 11/0005 |
| 2020/0371525 A1* | 11/2020 | Mizukami | .............. | A63H 3/445 |
| 2021/0023704 A1* | 1/2021 | Totsuka | ................. | B25J 9/1664 |
| 2021/0103281 A1* | 4/2021 | Takagi | ..................... | B25J 13/08 |
| 2021/0137438 A1* | 5/2021 | Salfity | ................. | G06V 40/174 |

FOREIGN PATENT DOCUMENTS

| | | | |
|---|---|---|---|
| CN | 108536802 A | | 9/2018 |
| CN | 108614987 A | | 10/2018 |
| CN | 109108961 A | | 1/2019 |
| EP | 3456487 A2 | | 3/2019 |
| JP | 2006-123136 A | | 5/2006 |
| JP | 2008-000157 A | | 1/2008 |
| JP | 2011000681 A | * | 1/2011 |
| JP | 2016012340 A | * | 1/2016 |
| JP | 2019-008510 A | | 1/2019 |
| WO | WO-2016092946 A1 | | 6/2016 |
| WO | 2017/175559 A1 | | 10/2017 |

OTHER PUBLICATIONS

International Search Report and Written Opinion of PCT Application No. PCT/JP2020/005680, issued on Mar. 24, 2020, 09 pages of ISRWO.

* cited by examiner

FIG.4

| NAME | AGE | GENDER | STATUS | TIME ZONE OF APPEARANCE | DURATION OF COMMUNICATION | RELATIONSHIP WITH OTHER USERS |
|---|---|---|---|---|---|---|
| A | 35 | MALE | ABSENT | 18:00~23:00 | 100 HOURS | HUSBAND OF B |
| B | 34 | FEMALE | PRESENT | 12:00~18:00 | 50 HOURS | WIFE OF A |
| C | 5 | MALE | PRESENT | 15:00~19:00 | 90 HOURS | CHILD OF A AND B |

FIG.5

| STATUS No. | TIME STAMP | OUTPUT OF ROBOT DEVICE | USER | USER STATE OR ACTION | ESTIMATED EMOTION OF USER |
|---|---|---|---|---|---|
| 1 | 18:15:01 | APPROACH | A | WATCHING TV | - |
| 2 | 18:15:10 | - | A | TOUCH ROBOT DEVICE | JOY |
| 3 | 18:16:30 | GAZE | B | - | - |
| 4 | 18:16:45 | - | B | TALK TO ROBOT DEVICE | JOY |
| 5 | 18:20:11 | APPROACH | C | STUDYING | - |
| 6 | 18:23:20 | - | C | BRUSH OFF ROBOT DEVICE | SURPRISE |
| ... | ... | ... | ... | ... | ... |

FIG.6

| USER | OUTPUT OF ROBOT DEVICE | ACTION OF USER | EMOTION OF USER | PRECONDITION |
|---|---|---|---|---|
| A | APPROACH | TOUCH ROBOT DEVICE | JOY | WHEN USER IS NOT PERFORMING ACTIVE WORK |
| B | GAZE | TALK TO ROBOT DEVICE | JOY | WHEN ROBOT DEVICE IS PRESENT WITHIN VISUAL FIELD OF USER |
| C | APPROACH | BRUSH OFF ROBOT DEVICE | SURPRISE | WHEN BEING TOGETHER WITH USER B |
| ... | ... | ... | ... | ... |

FIG.12

| | OUTPUT OF ROBOT DEVICE | ACTION OF USER | EMOTION OF USER | STATUS | |
|---|---|---|---|---|---|
| | | | | TIME ZONE | SURROUNDING ENVIRONMENT |
| SELECTED INTERACTION INFORMATION | APPROACH | TOUCH ROBOT DEVICE | JOY | MORN-ING | USER A IS IN NEIGHBORHOOD |
| GENERATED INTERACTION INFORMATION | APPROACH | BRUSH OFF ROBOT DEVICE | ANGER | MORN-ING | USER B IS IN NEIGHBORHOOD |

FIG.13

| | OUTPUT OF ROBOT DEVICE | ACTION OF USER | EMOTION OF USER | PRECONDITION |
|---|---|---|---|---|
| FIRST INTERACTION INFORMATION | APPROACH | TOUCH ROBOT DEVICE | JOY | USER A IS IN NEIGHBORHOOD |
| SECOND INTERACTION INFORMATION | APPROACH | BRUSH OFF ROBOT DEVICE | ANGER | USER B IS IN NEIGHBORHOOD |

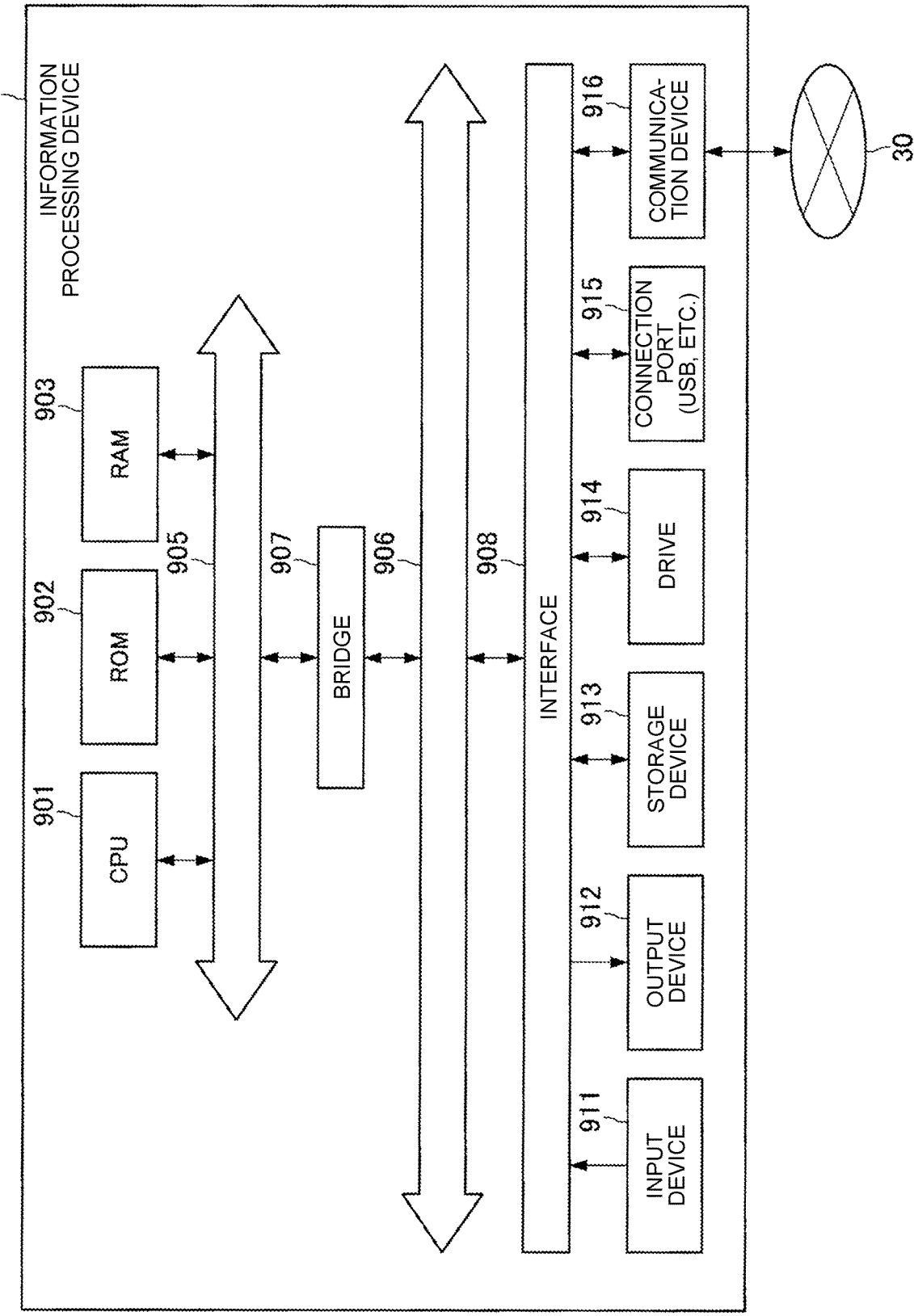

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2020/005680 filed on Feb. 14, 2020, which claims priority benefit of Japanese Patent Application No. JP 2019-077700 filed in the Japan Patent Office on Apr. 16, 2019. Each of the above-referenced applications is hereby incorporated herein by reference in its entirety.

FIELD

The present disclosure relates to an information processing device, an information processing method, and a program.

BACKGROUND

In recent years, robot devices that communicate with users have been becoming widespread. With this trend, such a robot device is required to have a technique for achieving more smooth communication with a user.

For example, Patent Literature 1 below discloses an action control technique of emulating human-like or bio-like actions by a robot device to increase empathy in a user for the robot device. Specifically, Patent Literature 1 discloses a technique of evaluating the degree of intimacy between a user and the robot device based on the number of times of contact from the user to the robot device or the like to control the robot device so as to move away from a user with low degree of intimacy and to approach a user with high degree of intimacy.

CITATION LIST

Patent Literature

Patent Literature 1: WO 2017/175559 A

SUMMARY

Technical Problem

However, the technique disclosed in Patent Literature 1 described above controls the distance of the robot device to the user, and thus would not be effective in improving the quality of communication between the user and the robot device. In addition, not only the robot device but also an agent that communicates with the user, a smart speaker, or the like has been required to improve the quality of communication between these devices and the user.

Therefore, there has been a demand for a technology capable of providing a user with higher quality communication by further enhancing interaction between the user and the interaction device.

Solution to Problem

According to the present disclosure, an information processing device is provided that includes: an output control unit that controls an output from an interaction device to a user; an action evaluation unit that determines an action of the user performed in correspondence with an output of the interaction device; an emotion estimation unit that estimates an emotion of the user corresponding to the action of the user; and an information accumulation unit that accumulates the output of the interaction device, the action of the user, and the emotion of the user in association with each other as interaction information, wherein the output control unit controls the output from the interaction device to the user based on the interaction information accumulated.

Moreover, according to the present disclosure, an information processing method to be executed by an arithmetic processing device is provided that includes: controlling an output from an interaction device to a user; determining an action of the user performed in correspondence with an output of the interaction device; estimating an emotion of the user corresponding to the action of the user; and accumulating the output of the interaction device, the action of the user, and the emotion of the user in association with each other as interaction information, and controlling the output from the interaction device to the user based on the interaction information accumulated.

Furthermore, according to the present disclosure, a program is provided that causes a computer to function as units including: an output control unit that controls an output from an interaction device to a user; an action evaluation unit that determines an action of the user performed in correspondence with an output of the interaction device; an emotion estimation unit that estimates an emotion of the user corresponding to the action of the user; and an information accumulation unit that accumulates the output of the interaction device, the action of the user, and the emotion of the user in association with each other as interaction information, and the program further causing the output control unit to function so as to control the output from the interaction device to the user based on the interaction information accumulated.

BRIEF DESCRIPTION OF DRAWINGS

FIG. 4 is a table illustrating an example of preset information related to a user.

FIG. 5 is a table illustrating an example in which outputs of a robot device and actions of the user are listed in the same time series.

FIG. 6 is a table illustrating an example of interaction information generated by an information accumulation unit.

FIG. 12 is a table illustrating an example of generated interaction information and selected interaction information.

FIG. 13 is a table illustrating an example of interaction information stored based on an example illustrated in FIG. 12.

FIG. 15 is a block diagram illustrating an example of a hardware configuration in an information processing device constituting a system according to embodiments of the present disclosure.

DESCRIPTION OF EMBODIMENTS

A preferred embodiment of the present disclosure will be described in detail hereinbelow with reference to the accompanying drawings. Note that redundant descriptions will be omitted from the present specification and the drawings by assigning the same reference signs to components having substantially the same functional configuration.

Note that the description will be provided in the following order.
1. Outline of technology according to present disclosure
2. First Embodiment
2.1. Configuration of information processing device
2.2. Operation of information processing device
2.3. Modification
3. Second Embodiment
3.1. Configuration of information processing device
3.2. Operation of information processing device
3.3. Application examples
4. Hardware configuration

1. Outline of Technology According to Present Disclosure

Figure 1:
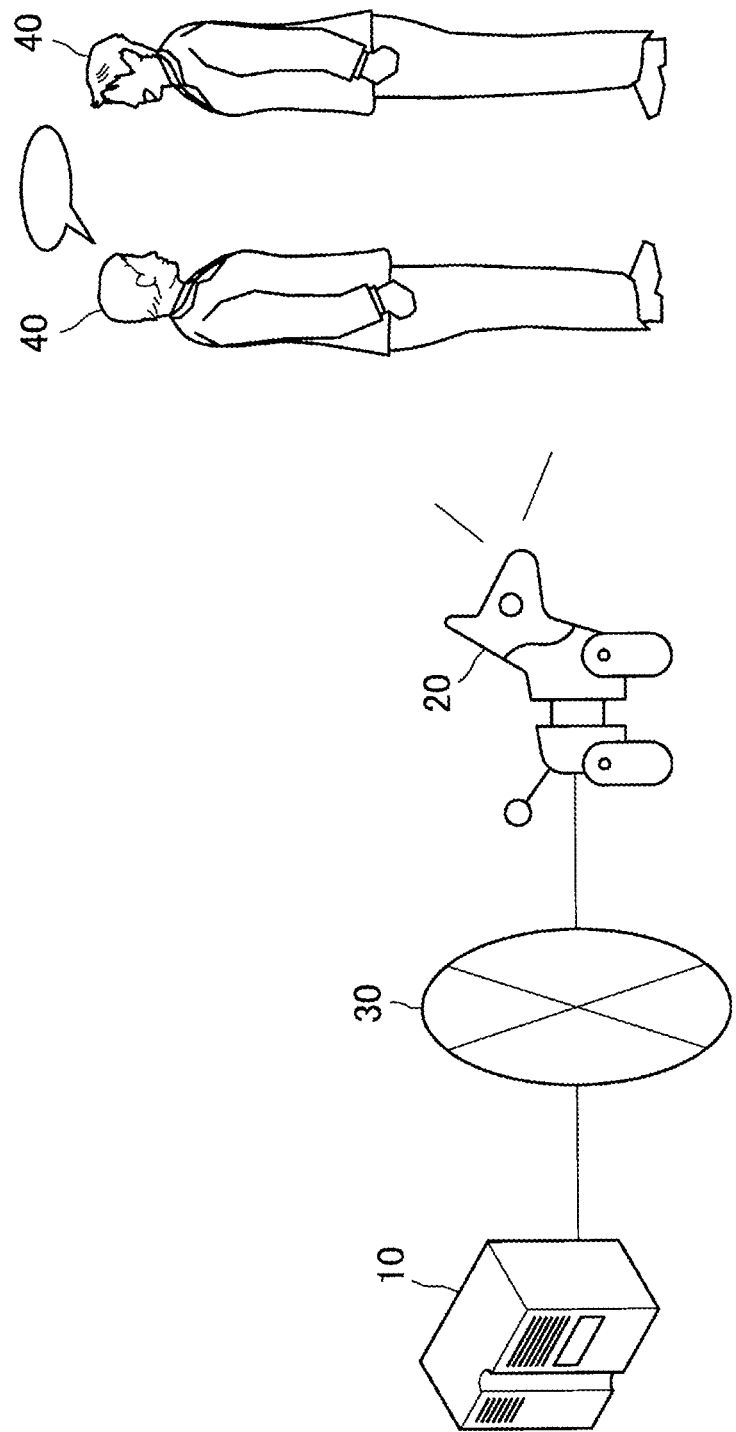
FIG. 1 is a diagram illustrating an outline of a system to which a technology according to the present disclosure is applied.

First, an outline of a system to which the technology according to the present disclosure is applied will be described with reference to FIG. 1. FIG. 1 is a diagram illustrating an outline of a system to which a technology according to the present disclosure is applied.

As illustrated in FIG. 1, a system to which the technology according to the present disclosure is applied includes an information processing device 10 and a robot device 20 connected to the information processing device 10 via a network 30. Although FIG. 1 illustrates two users 40 as the users of the robot device 20, the number of users of the robot device 20 may unquestionably be one or three or more.

The robot device 20 is an autonomous action robot device capable of interacting with the user 40. The robot device 20 is a robot device that operates in the neighborhood of the user 40, and may be a pet-shaped robot, a humanoid communication robot, a transfer robot, or an articulated robot, for example.

By controlling actions of the robot device 20 based on an external environment observation result obtained by an imaging device, a microphone, or various sensors, it is possible to allow the robot device 20 to interact with the user 40. The robot device 20 may interact with the user 40, for example, by output of sound or other output including image display, movement, or operation.

However, in the system to which the technology according to the present disclosure is applied, the device that interacts with the user 40 may unquestionably be a device other than the robot device 20. For example, a system to which the technology according to the present disclosure is applied may include, instead of the robot device 20, a display device that visually outputs an agent imitating a character or a personality, or a sound output device that aurally outputs an utterance of the agent. In the present specification, a group of such devices that interact with the user 40 including the robot device 20 is also referred to as an interaction device.

The network 30 is a wired or wireless transmission path of information. For example, the network 30 may be a public network such as the Internet, a telephone network, and a satellite communication network, or various local area networks (LANs) including Ethernet (registered trademark), wide area networks (WANs), or the like. Furthermore, the network 30 may be a dedicated network such as an Internet protocol-virtual private network (IP-VPN).

Note that the information processing device 10 and the robot device 20 may be directly connected to each other without the network 30. For example, the information processing device 10 and the robot device 20 may be connected to each other by wired communication, or may be connected to each other by wireless communication using Wi-Fi (registered trademark) or Bluetooth (registered trademark).

The information processing device 10 controls details of interaction between the robot device 20 and the user 40. Specifically, the information processing device 10 controls an output from the robot device 20 to the user 40 based on a sensing result regarding a space in which the user 40 exists. Specifically, the information processing device 10 may estimate an output expected or requested by the user 40 to the robot device 20 based on the details of the sensed utterance or action of the user 40, and may control the robot device 20 to give the estimated output.

For example, the information processing device 10 may generate an answer to a question uttered by the user 40 and may allow the robot device 20 to output the generated answer as a voice or an image. Alternatively, the information processing device 10 may control the action of the robot device 20 so as to perform an action that attracts the interest or attention of the user 40.

With a system to which the technology according to the present disclosure is applied, the information processing device 10 analyses information related to the space in which the user 40 exists and then controls the details of an output from the robot device 20 based on a result of the analysis, enabling bidirectional communication between the robot device 20 and the user 40. For example, the system to which the technology according to the present disclosure is applied can allow the robot device 20 and the user 40 to have a conversation or a response, allow the robot device 20 to perform an operation of emulating a pet, or allow the robot device 20 and the user 40 to work together.

The technology according to the present disclosure accumulates, in such a system, an output of the robot device 20 to the user 40 and an action and emotion of the user 40 in correspondence with the output, in association with each other.

With the technology according to the present disclosure, since the information processing device 10 can estimate the reaction of the user 40 to the output of the robot device 20 by using the information accumulated as above, it is possible to further improve the quality of communication from the robot device 20 to the user 40.

Furthermore, according to the technology of the present disclosure, when it is desired to induce a predetermined action or emotion in the user 40, the information processing device 10 can determine the output of the robot device 20 corresponding to the action or emotion to be induced, by using the information accumulated as above. Accordingly, the information processing device 10 can induce a predetermined action or emotion in the user 40 via the robot device 20.

2. First Embodiment (2.1. Configuration of Information Processing Device)

Figure 2:
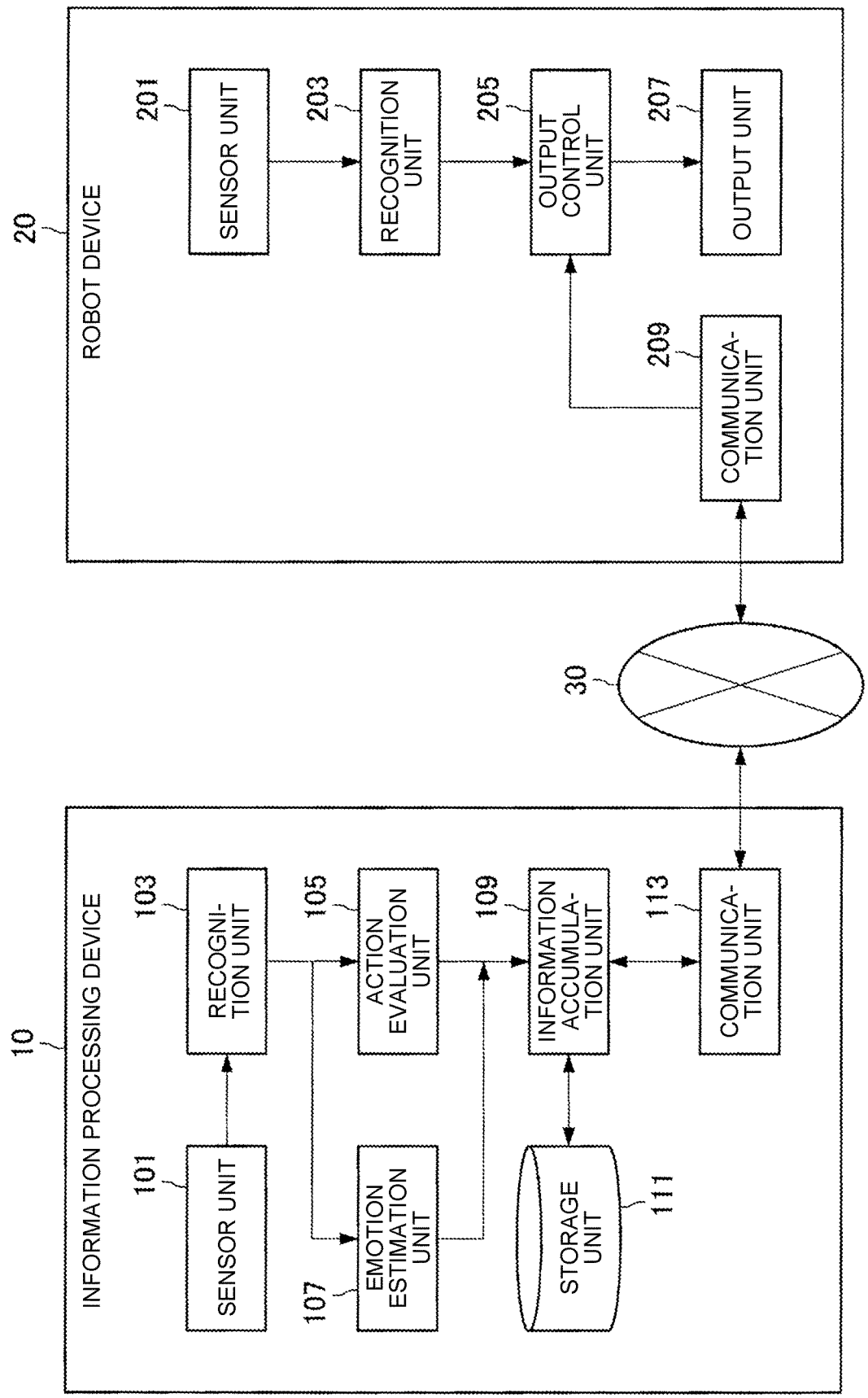
FIG. 2 is a block diagram illustrating a functional configuration of a system according to a first embodiment of the present disclosure.

Hereinafter, a first embodiment that implements the above-described technology according to the present disclosure will be described with reference to FIG. 2. FIG. 2 is a block diagram illustrating a functional configuration of a system according to the first embodiment.

As illustrated in FIG. 2, the system according to the present embodiment includes an information processing device 10 and a robot device 20 connected to each other via a network 30.

The robot device 20 gives an output having details determined by the information processing device 10 to the user 40 based on the sensing result regarding the space in which the user 40 exists. Here, the output of the robot device 20 represents various types of stimuli to at least one or more of visual, auditory, or tactile senses from the robot device 20 to the user 40. For example, the output of the robot device 20 may represent any output from the robot device 20 to the user 40, such as image display, sound output, motion presentation, movement such as approach or separation, transfer of an object, and contact.

(Information Processing Device 10)

The information processing device 10 includes a sensor unit 101, a recognition unit 103, an action evaluation unit 105, an emotion estimation unit 107, an information accumulation unit 109, a storage unit 111, and a communication unit 113.

The information processing device 10 may be an information processing device that does not receive a direct stimulus from the user 40, such as a control device of a monitoring camera system, for example, or may be an information processing device that receives a direct stimulus from the user 40, such as a smart speaker. Furthermore, the information processing device 10 may be a computer or the like that does not include the sensor unit 101 and performs information processing alone.

The sensor unit 101 includes a sensor that acquires information related to a space in which the user 40 exists.

For example, the sensor unit 101 includes various cameras such as an RGB camera, a grayscale camera, a depth camera, an infrared camera, or a time of flight (ToF) camera, and may acquire a photographic image of a space in which the user 40 exists. The sensor unit 101 may further acquire information related to the distance to an object such as the user 40 by including a plurality of these various cameras. Furthermore, the sensor unit 101 includes various distance measuring sensors such as a laser imaging detection and ranging (LIDAR) sensor or a radio detecting and ranging (RADAR) sensor, and may acquire information regarding arrangement of objects in a space where the user 40 exists. Furthermore, the sensor unit 101 may include a microphone to acquire a voice in a space where the user 40 exists so as to acquire information related to the position and status of the user 40. The sensor unit 101 may include a plurality of microphones to further acquire information specifying the sound source position. In addition, the sensor unit 101 may include a sensor such as an illuminometer, a thermometer, or a hygrometer so as to acquire information related to the environment of the space in which the user 40 exists.

However, the sensor unit 101 may unquestionably include a known sensor other than the above-described sensor as long as it can acquire information related to the space in which the user 40 exists.

The recognition unit 103 recognizes the status of the space in which the user 40 exists based on the information acquired by the sensor unit 101. Specifically, the recognition unit 103 may recognize the status of the space by applying image recognition based on a predetermined rule or a machine learning algorithm on a photographic image of the space in which the user 40 exists, acquired by various cameras of the sensor unit 101.

Figure 3:
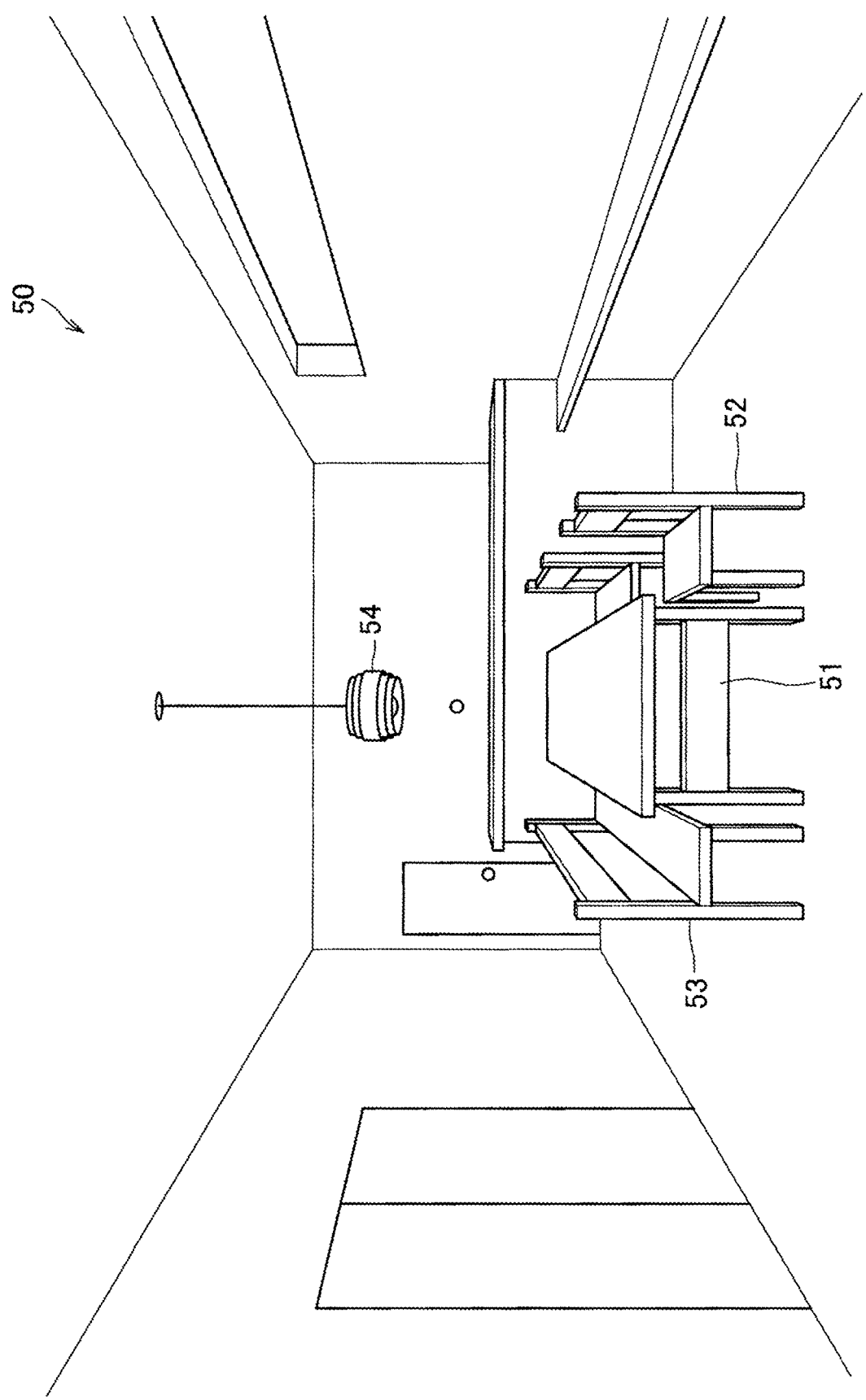
FIG. 3 is a schematic diagram illustrating an example of a photographic image of a typical indoor space.

For example, when a photographic image illustrated in FIG. 3 is acquired by various cameras included in the sensor unit 101, the recognition unit 103 may recognize the type, number, position, or the like of the object in the space captured in the photographic image based on an object recognition algorithm.

FIG. 3 is a schematic diagram illustrating an example of a photographic image of a typical indoor space. As illustrated in FIG. 3, it is assumed that a table 51, chairs 52 and 53, and an indoor light 54 are present in an indoor space 50, for example.

The recognition unit 103 may recognize the objects that have been set as the table 51, the chairs 52 and 53, or the indoor light 54 by the user 40 living in the indoor space 50 based on their features such as shape or color, and may thereby recognize the position or the like of the object in the indoor space 50 captured in the photographic image. Alternatively, the recognition unit 103 may recognize the table 51, the chairs 52 and 53, and the indoor light 54 individually from among the objects existing in the indoor space 50 using an algorithm constructed by supervised machine learning.

Furthermore, the recognition unit 103 may further perform personal and positional recognition of the user 40 in the space. Specifically, the recognition unit 103 may apply an algorithm based on a preset feature amount or machine learning on the photographic image to perform facial recognition of the user 40 so as to perform personal and positional recognition of the user 40. Alternatively, the recognition unit 103 may recognize the gender and the age of the user 40 from the voice or physical characteristics so as to perform personal and positional recognition of the user 40 by comparing the recognized gender and age of the user 40 with preset information relate to the user 40.

Incidentally, examples of the preset information related to the user 40 include pieces of information as illustrated in FIG. 4. FIG. 4 is a table illustrating an example of preset information related to the user 40 in the information processing device 10.

As illustrated in FIG. 4, as the information related to the user 40, the information processing device 10 may store the name, age and gender of the user 40, and the relationship with another user, for each of users. Furthermore, the information processing device 10 may store the presence or absence of the user 40 in the space at a point sensed by the sensor unit 101 based on the recognition obtained by the recognition unit 103. Furthermore, the information processing device 10 may store a time zone in which the user 40 is highly likely to be present in the space as frequent occurrence time based on the sensing result obtained by the sensor unit 101. In addition, the information processing device 10 may store a duration of communication time between the user 40 and the robot device 20.

Furthermore, the recognition unit 103 may further perform positional and personal recognitions of the robot device 20 in the space. Specifically, the recognition unit 103 may perform positional and personal recognitions of the robot device 20 by recognizing the shape of the robot device 20 captured in the photographic image or the identification two-dimensional code or the identification number affixed to the robot device 20.

The action evaluation unit 105 grasps the action of the user 40 in the space based on the information acquired by the sensor unit 101. Specifically, the action evaluation unit 105 may grasp the action of the user 40 based on the photographic image of the user 40 acquired by the sensor unit 101. Furthermore, the action evaluation unit 105 may grasp an utterance message of the user 40 based on the voice information of the user 40 acquired by the sensor unit 101.

For example, the action evaluation unit 105 may grasp the action or state of the user 40 at a point of the output given by the robot device 20 to the user 40 together with the time of day. Furthermore, when the action or state of the user 40 has changed, the action evaluation unit 105 may grasp the action or state of the user after the change together with the time of day. By grasping the action or state of the user 40 at such timing, the action evaluation unit 105 can determine the action of the user 40 performed in correspondence with the output of the robot device 20 without constantly grasping the action or state of the user 40.

Furthermore, the action evaluation unit 105 determines an action of the user 40 performed in correspondence with the output of the robot device 20. Specifically, by listing the outputs from the robot device 20 to the user 40 and the actions of the user 40 in the same time series, the action evaluation unit 105 can determine the actions of the user 40 performed in correspondence with the output of the robot device 20.

For example, when the action of the user 40 is performed within a predetermined time continuously to the output from the robot device 20 to the user 40, the action evaluation unit 105 may determine that the output of the robot device 20 corresponds to the action of the user 40. Furthermore, when the action of the user 40 has been changed after the output from the robot device 20 to the user 40, the action evaluation unit 105 may determine that the output of the robot device 20 corresponds to the action of the user 40 after the change. This is because it is considered that the user 40 has changed the action in order to achieve correspondence with the output from the robot device 20 to the user 40. Furthermore, when an identical combination of the output from the robot device 20 to the user 40 and the action of the user 40 is confirmed a plurality of times, the action evaluation unit 105 may determine the correspondence between the output of the robot device 20 and the action of the user 40.

Furthermore, at an occurrence of a direct action from the user 40 toward the robot device 20, when the output of the robot device 20 takes time, or the action of the user 40 takes time, the action evaluation unit 105 may determine the correspondence between the output of the robot device 20 and the action of the user 40 in consideration of the lapse of time between the output of the robot device 20 and the action of the user 40.

Note that the action evaluation unit 105 may also grasp information other than the above-described information as long as the information can be grasped based on the action of the user 40. For example, when it is possible to grasp the relationship among the plurality of users 40 based on the frequency or message of the utterance of the user 40, the positional relationship of the user 40, or the target or details of the action of the user 40, the action evaluation unit 105 may grasp the relationship among the plurality of users 40 based on the utterance or the action of the user 40. These pieces of information grasped by the action evaluation unit 105 may be stored in the information processing device 10 by being added to the information regarding the user 40 illustrated in FIG. 4.

The emotion estimation unit 107 estimates an emotion of the user 40 corresponding to an action of the user 40. Specifically, initially, the emotion estimation unit 107 has preliminary settings of an evaluation axis of the emotion and an action of the user 40 related to the emotion of the evaluation axis. With this setting, the emotion estimation unit 107 can estimate the emotion of the user 40 by comparing the action of the user 40 grasped by the action evaluation unit 105 with the action set for each of emotions on the evaluation axis. Examples of the emotion evaluation axis include surprise, fear, sadness, and joy.

Furthermore, when biological information such as the heart rate, the blood pressure, or the body temperature of the user 40 can be acquired from various cameras included in the sensor unit 101, a wearable terminal worn by the user 40, or the like, the emotion estimation unit 107 may estimate the emotion of the user 40 based on the biological information of the user 40. In such a case, the emotion estimation unit 107 may estimate the emotion of the user 40 by comparing the state of the user 40 indicated by the biological information with the state set in advance for each of emotions on the evaluation axis.

Here, specific examples of the operations of the action evaluation unit 105 and the emotion estimation unit 107 will be described with reference to FIG. 5. FIG. 5 is a table illustrating an example in which outputs of the robot device 20 and actions of the user 40 are listed in the same time series.

As illustrated in FIG. 5, time stamps are attached to the outputs of the robot device 20 and the actions of the user 40 on the same clock, making it possible to list the outputs of the robot device 20 and the actions of the user 40 in the same time series.

For example, the table illustrated in FIG. 5 indicates, as status No. 1, that the robot device 20 has output "approaching" to a user "A" in a state "watching TV" at "18:15:01". Subsequently, it indicates, as status No. 2, that the user "A" has performed an action of "touching the robot device" on "18:15:10". Next, it indicates, as status No. 3, that the robot device 20 has output "gazing" at a user "B" on "18:16:30". Furthermore, it indicates, as status No. 4, that the user "B" has performed an action of "talking to the robot device" on "18:16:45". In addition, it indicates, as status No. 5, that the robot device 20 outputs "approaching" a user "C" in a state "studying" on "18:20:11". Subsequently, it indicates, as status No. 6, that the user "C" has performed an action "brushing off the robot device" on "18:23:20".

In such a case, the action evaluation unit 105 may determine that there is a correspondence between the output of the robot device 20 of status No. 3 and the action of the user 40 of status No. 4, which have the same target users 40 and close occurrence times. Furthermore, the action evaluation unit 105 may determine that there is a correspondence between the output of the robot device 20 of status No. 1 and the action of the user 40 of status No. 2, which have the same target user 40 and which indicate a change in the state or action of the user 40 after the output from the robot device 20. Furthermore, the action evaluation unit 105 may determine that there is a correspondence between the output of the robot device 20 of status No. 5 and the action of the user 40 of status No. 6, which have the same target user 40 and which indicate a change in the state or action of the user 40 after the output from the robot device 20, even though their occurrence times of day are not close.

Furthermore, the table illustrated in FIG. 5 illustrates each of the emotions of the user 40 estimated by the emotion estimation unit 107 from the actions of the users 40 in status Nos. 2, 4, and 6 determined to correspond to the outputs of the robot device 20. For example, an emotion of "joy" is estimated from the action "touching the robot device" performed by the user "A" in status No. 2. Furthermore, an emotion of "joy" is estimated from the action "talking to the robot device" performed by the user "B" in status No. 4. Furthermore, the emotion of "surprise" is estimated from the action "brushing off the robot device" performed by the user "C" in status No. 6.

The information accumulation unit 109 accumulates the output of the robot device 20, the action of the user 40 corresponding to the output of the robot device 20, and the emotion of the user 40 estimated from the action of the user 40 in association with each other as interaction information. Specifically, the information accumulation unit 109 generates the interaction information for each of the users 40 by combining the output of the robot device 20, the action of the user 40, and the emotion of the user 40 estimated from the action of the user 40 by the emotion estimation unit 107, which are determined to correspond to each other by the action evaluation unit 105.

The generated interaction information may be accumulated in the storage unit 111 to construct a database, for example. The storage unit 111 may be actualized by, for example, a magnetic storage device such as a hard disk drive (HDD), a semiconductor storage device such as a solid state drive (SSD), an optical storage device, a magneto-optical storage device, or the like.

For example, the information accumulation unit 109 can generate the interaction information illustrated in FIG. 6 from the specific example illustrated in FIG. 5. FIG. 6 is a table illustrating an example of interaction information generated by the information accumulation unit 109.

As illustrated in FIG. 6, for example, the information accumulation unit 109 can generate, regarding the "user A", interaction information in which the output of the robot device 20 of "approaching", the action of the user 40 of "touching the robot device", and the emotion of the user 40 of "joy" are associated with each other, based on the information of status Nos. 1 and 2 in FIG. 5. Furthermore, the information accumulation unit 109 can generate, regarding the "user B", interaction information in which the output of the robot device 20 of "gazing", the action of the user 40 of "talking to the robot device", and the emotion of the user 40 of "joy" are associated with each other, based on the information of the status Nos. 3 and 4 in FIG. 5. Furthermore, the information accumulation unit 109 can generate, regarding the "user C", interaction information in which the output of the robot device 20 of "approaching", the action of the user 40 of "brushing off the robot device", and the emotion of the user 40 of "surprise" are associated with each other, based on the information of the status Nos. 5 and 6 in FIG. 5.

The information accumulation unit 109 generates interaction information every time the action evaluation unit 105 grasps a combination of the output from the robot device 20 to the user 40 and the action of the user 40 corresponding to the output from the robot device 20. With this configuration, the information accumulation unit 109 can generate a database including the reactions of the user 40 to the outputs from the robot device 20 as the interaction information. Accordingly, when there is an output from the robot device 20 to the user 40, the information processing device 10 can search for the reaction of the user 40 for the similar output from among the accumulated interaction information, enabling prediction of the reaction of the user 40.

Furthermore, the information accumulation unit 109 may add, to the interaction information, preconditions regarding an environment or the like at the occurrence of a combination of the output of the robot device 20 and the action of the user 40. This is because even when the same output is given from the robot device 20 to the user 40, the reaction of the user 40 might be different.

In an assumable exemplary case where the robot device 20 approaches the user 40, the user 40 normally gives a reaction of stroking the robot device 20. However, when the user 40 does not notice the robot device 20 or performs other works, the user 40 would not always give a reaction of stroking the robot device 20 even when the robot device 20 approaches the user 40. The information accumulation unit 109 can classify, as the preconditions, situational differences in actions of the user 40 in response to the output of the robot device 20 so as to improve the accuracy of the interaction information.

For example, in the specific example of the interaction information illustrated in FIG. 6, a precondition "when the user is not performing active work" is added to the interaction information in which the action of the user 40 "touching the robot device" is associated with the output of the robot device 20 "approaching". Furthermore, a precondition "when the robot device is present within the visual field of the user" is added to the interaction information in which the action of the user 40 "talking to the robot device" is associated with the output "gazing" from the robot device 20. Furthermore, a precondition of "when being together with the user B" is added to the interaction information in which the action of the user 40 "brushing off the robot device" is associated with the output "approaching" from the robot device 20.

These preconditions are set by the information accumulation unit 109 based on difference in reactions from the user 40 when the same output is given from the robot device 20 to the user 40. Here is an assumable exemplary case where, after accumulation of the interaction information in which the output of "approaching" from the robot device 20 to the user 40 and the action of the user 40 of "stroking" are associated with each other, an action of the user 40 of "brushing off" is induced in correspondence with the output of "approaching" from the robot device 20 to the user 40. At this time, in individual cases, the information accumulation unit 109 extracts a difference in the individual cases by referring to the time zone of occurrence of the action of the user 40, the state of the user 40, or the state of the environment around the user 40. Thereafter, the information accumulation unit 109 can add the extracted difference as a precondition to the interaction information corresponding to the individual cases.

The communication unit 113 is a communication interface for exchanging information between the information processing device 10 and the robot device 20.

For example, the communication unit 113 may exchange information between the information processing device 10 and the robot device 20 via the network 30. The network 30 may be a public communication network such as the Internet, a satellite communication network, or a telephone line network, or a communication network provided in a limited area, such as a local area network (LAN) or a wide area network (WAN).

Furthermore, the communication unit 113 may directly exchange information between the information processing device 10 and the robot device 20. For example, the communication unit 113 may exchange information between the information processing device 10 and the robot device 20 using wireless communication such as wireless LAN, Wi-Fi (registered trademark), or Bluetooth (registered trademark), or wired communication such as communication using a coaxial cable.

(Robot Device 20)

The robot device 20 includes a sensor unit 201, a recognition unit 203, an output control unit 205, an output unit 207, and a communication unit 209.

The robot device 20 is, for example, a robot device capable of autonomous action. Specifically, the robot device 20 may be an animal-shaped or humanoid robot capable of performing communication with the user 40, or may be a transfer robot capable of performing cooperative work with the user 40, an articulated robot, or the like.

The sensor unit 201 includes a sensor that acquires external environment information of the robot device 20 and a sensor that acquires own information of the robot device 20. For example, as sensor that acquire external environment information of the robot device 20, the sensor unit 201 may include various cameras such as an RGB camera, a grayscale camera, a stereo camera, a depth camera, an infrared camera, or a ToF camera, various distance measuring sensors such as a LIDAR sensor and a RADAR sensor, or a sensor such as a microphone, an illuminometer, a thermometer, or a hygrometer. In addition, the sensor unit 201 may include, as a sensor that acquires own information of the robot device 20, for example, an encoder, a voltmeter, an ammeter, a strain gauge, a pressure gauge, an inertial measurement unit (IMU), or the like. The information acquired by the various sensors included in the sensor unit 201 is used to control the output of the robot device 20.

However, the sensor unit 201 may unquestionably include a known sensor other than the above-described sensor as long as it can acquire environmental information regarding the surroundings of the robot device 20 or own information of the robot device 20.

The recognition unit 203 recognizes an external environmental state of the robot device 20 or an own device state of the robot device 20 based on the information acquired by the sensor unit 201. Specifically, the recognition unit 203 may recognize the external environment state of the robot device 20 by performing object recognition, motion recognition, text recognition, or voice recognition based on the environment information acquired by the sensor unit 201. Furthermore, the recognition unit 203 may recognize the own state of the robot device 20 by performing position recognition, motion state (for example, velocity, acceleration, jerk, angular velocity, angular acceleration, or the like) recognition, or device body state (for example, the remaining power, temperature, joint angle, or the like) recognition based on the own device information acquired by the sensor unit 201.

The recognition by the recognition unit 203 can be performed by using any known recognition technology. The recognition by the recognition unit 203 may be performed, for example, based on a predetermined rule or based on a machine learning algorithm.

The output control unit 205 controls an output to be given from the robot device 20 to the user 40. Specifically, the output control unit 205 generates an output to be given to the user 40 based on the accumulated interaction information, and further generates a control command for actualizing the output.

For example, based on the accumulated interaction information, the output control unit 205 may generate an output from the robot device 20 corresponding to an action or emotion desired to be induced in the user 40, and may further generate a control command for actualizing the output. When controlling to give an output to induce a predetermined emotion in the user 40 from the robot device 20, the output control unit 205 can extract an output that can induce the predetermined emotion in the user 40 by referring to the accumulated interaction information, enabling generation of a control command for actualizing the output to be given from the robot device 20 to the user 40.

Note that part or all of the functions of the output control unit 205 may be provided in the information processing device 10 instead of the robot device 20.

The output unit 207 generates an output from the robot device 20 to the user 40 based on a control command from the output control unit 205. Specifically, the output unit 207 may be any module as long as the module performs output to the real space. For example, the output unit 207 may be devices such as an actuator referred to as a magnetic motor or a fluid pump, a power device such as an engine, a speaker that outputs sound, a projector that outputs an image, a display, a light emitter (for example, a light bulb, an LED, a laser, or the like).

The communication unit 209 is a communication interface for exchanging information between the information processing device 10 and the robot device 20. Specifically, the communication unit 209 may be a communication interface corresponding to the communication unit 113 of the information processing device 10.

For example, the communication unit 209 may exchange information between the information processing device 10 and the robot device 20 via the network 30. The network 30 may be a public communication network such as the Internet, a satellite communication network, or a telephone line network, or a communication network provided in a limited area, such as a local area network (LAN) or a wide area network (WAN).

Furthermore, the communication unit 209 may directly exchange information between the information processing device 10 and the robot device 20. For example, the communication unit 209 may exchange information between the information processing device 10 and the robot device 20 using wireless communication such as wireless LAN, Wi-Fi (registered trademark), or Bluetooth (registered trademark), or wired communication such as communication using a coaxial cable.

The functional groups constituting the system according to the present embodiment have been specifically described above. These function groups are not limited to the examples described above, and may be included in either the information processing device 10 or the robot device 20. Furthermore, these functional groups may be integrated in the robot device 20.

(2.2. Operation of Information Processing Device)

Figure 7:
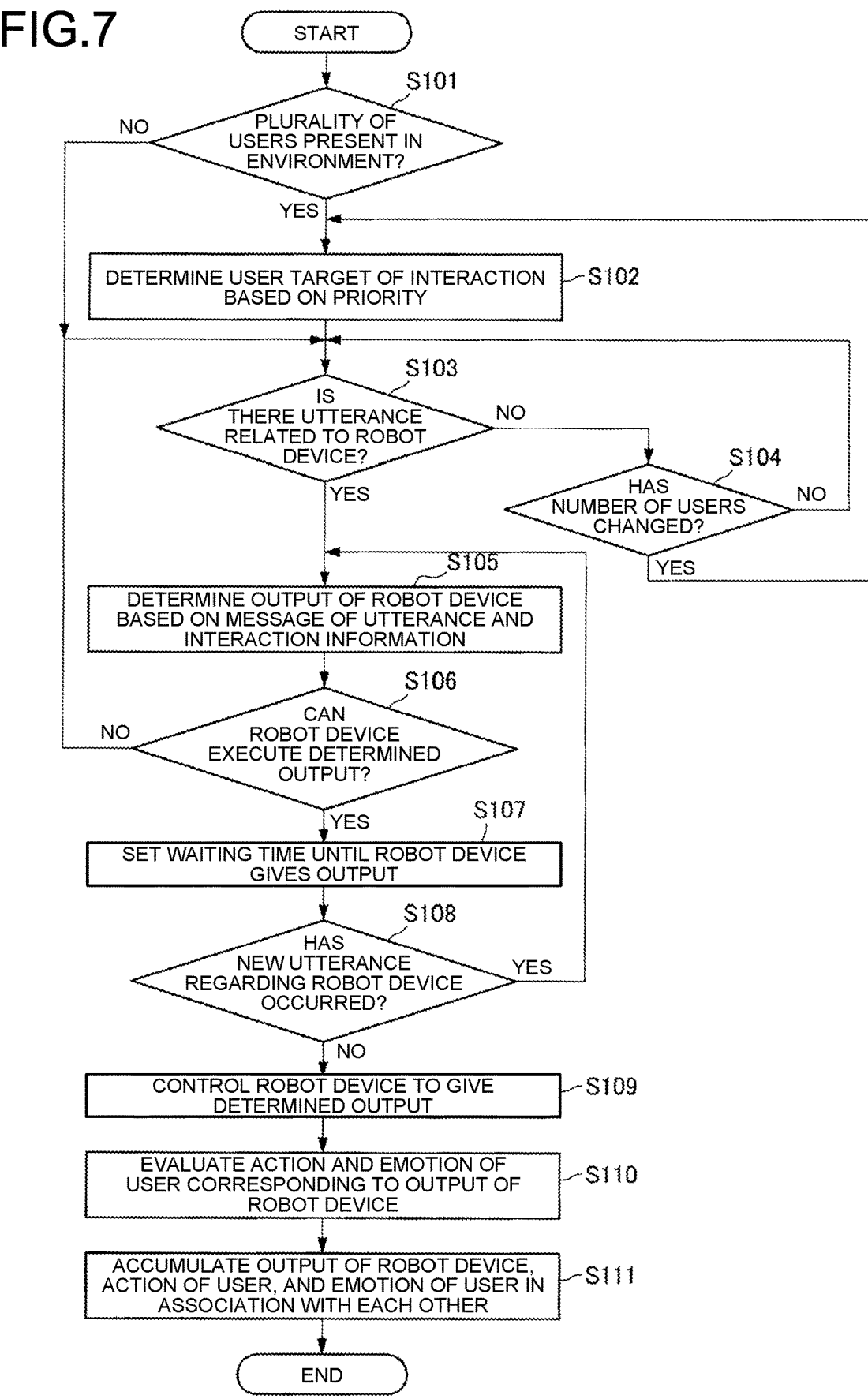
FIG. 7 is a flowchart illustrating an example of an operation executed by the system according to the embodiment.

Next, operations of the system according to the present embodiment will be described with reference to FIG. 7. FIG. 7 is a flowchart illustrating an example of an operation executed by the system according to the present embodiment.

The operation example according to the flowchart illustrated in FIG. 7 is an operation example for the purpose of improving the intimacy in the user 40 toward the robot device 20. The system according to the present embodiment grasps the utterance of the user 40 and allows the robot device 20 to give outputs based on the utterance message of the user 40, thereby enabling higher-quality interaction between the user 40 and the robot device 20. For example, the system according to the present embodiment allows the robot device 20 to give an output that is estimated to be expected from the robot device 20 by the user 40 based on the utterance message, making it possible to provide the user 40 with an experience of having mutual understanding with the robot device 20.

As illustrated in FIG. 7, first, the information processing device 10 determines whether or not a plurality of users 40 exist in the environment based on the sensing results in the environment from the sensor unit 101 (S101). The system according to the present embodiment associates the output of the robot device 20 with the action and emotion of the user 40 for each of users. Accordingly, with a plurality of users 40 present in the environment, the information processing device 10 first determines the user 40 to which the robot device 20 is to give an output.

when a plurality of users 40 exist in the environment (S101/Yes), the information processing device 10 determines the user 40 to which the robot device 20 is to give an output based on the priority set for each of the users 40 (S102).

The priority may be set based on the degree of interaction (also referred to as communication) between the user 40 and the robot device 20. For example, the priority may be set based on parameters such as the frequency, time, depth, or density of the interaction between the user 40 and the robot device 20 such that the higher the degrees of the parameters in the user 40, the higher priority will be assigned.

Here, when the user 40 is a user who has no experience of communicating with the robot device 20 and thus having no priority that has been set, the information processing device 10 may set the priority based on attribute information of the user 40. For example, the information processing device 10 may set the priority of making an output from the robot device 20 to the user 40 by generating an action model of the user 40 based on the age and gender of the user 40 estimated from the photographic image or the like.

When there is only one user 40 in the environment (S101/No), the information processing device 10 performs the operation of step S103 without performing the operation of step S102.

Subsequently, the information processing device 10 determines whether or not there is an utterance related to the robot device 20 in the utterance of the user 40 to which the robot device 20 is to give an output (S103). When there is no utterance related to the robot device 20 (S103/No), the information processing device 10 determines whether or not the number of users 40 in the environment has changed (S104), and then waits until the user 40 gives an utterance related to the robot device 20. However, when the number of users 40 in the environment has changed (S104/Yes), emergence of the user 40 with a higher priority could change the user 40 as a target to have an output. Therefore, the information processing device 10 returns to step S102 and performs the operations again.

Next, the information processing device 10 determines an output to be given from the robot device 20 to the user 40 based on a message of the utterance of the user 40. At this time, the information processing device 10 may modify the output to be performed from the robot device 20 to the user 40 to be a more suitable output based on the accumulated interaction information (S105).

For example, when the utterance of the user 40 indicates a message that specifically designates an output of the robot device 20 such as "would like the robot to come closer", the information processing device 10 can directly determine the output to be given from the robot device 20 to the user 40.

In another case where the utterance of the user 40 indicates a message of feeling or impression which does not specify the output of the robot device 20, such as "cute robot", the information processing device 10 may determine an output that would induce an emotion included in the utterance message of the user 40 as the output to be given to the user 40 based on the accumulated interaction information. For example, when the utterance of the user 40 includes a message of "Cute robot", the information processing device 10 may determine a plurality of patterns of outputs set as cute gestures to be used as outputs to be given by the robot device 20. Furthermore, it is allowable to set feasibility for each of the outputs of the plurality of determined patterns. With this configuration, by performing control such as reducing the feasibility of the output using the voice in a situation where the output of voice is restricted such as at night, the information processing device 10 can control the output of the robot device 20 in consideration of the external environment.

Even with these advantages, the technology according to the present embodiment is not limited to the above examples. The information processing device 10 can also estimate an output expected by the user 40 to the robot device 20 from the motion of the user 40 and determine an output to be given from the robot device 20 to the user 40.

Subsequently, the information processing device 10 determines whether or not the robot device 20 can execute the determined output (S106). For example, when the robot device 20 is a pet-shaped robot imitating an animal such as a dog, the robot device 20 has a walking mechanism, making it possible to give an output for realizing the utterance including a message "would like the robot to come closer". In contrast, such a robot device 20 does not have a flight mechanism, and thus it is not possible to give an output that realizes an utterance including a message "would like the robot to fly". In this manner, the information processing device 10 determines whether or not the robot device 20 can execute the determined output in consideration of the functionality of the robot device 20.

When the robot device 20 cannot execute the determined output (S106/No), the information processing device 10 returns to step S103 and waits until the user 40 gives an utterance related to the robot device 20.

In contrast, when the robot device 20 can execute the determined output (S106/Yes), the information processing device 10 sets a waiting time until the robot device 20 gives the output (S107). This setting is given because immediate reaction of the robot device 20 to the utterance of the user 40 would give the user 40 an impression that the robot device 20 takes a reflex action and automatic reaction, which would not be effective for development of emotions in the user 40. The length of the waiting time until the robot device 20 gives an output may be set based on the details of the output given by the robot device 20. For example, if the output given by the robot device 20 is direct movement or the like, the waiting time may be set to a short length. Furthermore, the length of the waiting time until the robot device 20 gives an output may be randomly set so as allow the user 40 to keep feeling fresh.

Here, when a new utterance related to the robot device 20 has occurred during the waiting time until the robot device 20 gives an output (S108/Yes), the information processing device 10 may return to step S105 and re-determine the output to be given by the robot device 20. Furthermore, although not illustrated, in an emergence of a user with a higher priority that can be a target to receive an output during the waiting time until the robot device 20 gives the output, the information processing device 10 may return to step S103 and re-determine the output to be given by the robot device 20.

When the waiting time has elapsed with no occurrence of events that would lead to redetermination of the output to be given by the robot device 20 (S108/No), the information processing device 10 controls the robot device 20 to give the determined output (S109). In this manner, the information processing device 10 can support interaction between the robot device 20 and the user 40 by performing control such that the robot device 20 gives an output estimated to be expected from the user 40 to the robot device 20 based on the utterance or action of the user 40.

Thereafter, the information processing device 10 evaluates the action and emotion of the user 40 corresponding to the output from the robot device 20 (S111). Specifically, the information processing device 10 determines the action of the user 40 performed in correspondence with the output from the robot device 20, and estimates the emotion of the user 40 from the action of the user 40.

Moreover, the information processing device 10 generates interaction information in which an output from the robot device 20, an action of the user 40 performed in correspondence with the output, and an emotion of the user 40 estimated from the action are associated with each other, and accumulates the generated interaction information (S113).

At this time, when the interaction information having the same output of the robot device 20 has already been accumulated, the information processing device 10 may further add a precondition to the interaction information by comparing the generated interaction information with the already accumulated interaction information.

For example, here is an assumable case where there has been an accumulation of interaction information indicating that an action of "smiling" and an emotion of "joy" in the user 40 are induced in correspondence with an output of "approaching" from the robot device 20 to the user 40. In this case, however, it is also assumable that, even with the same output by the robot device 20 in a situation where the user 40 is busy such as in the weekday morning, the action and emotion of the user 40 are more negative than what indicated in the accumulated interaction information. In such a case, the information processing device 10 can grasp that the negative action and emotion of the user 40 are induced in correspondence with the output of "approaching" of the robot device 20 on the precondition of the time zone of weekday morning. Therefore, by updating the accumulated interaction information based on the grasped information, the information processing device 10 can change the output to be given by the robot device 20 from "approaching" to other outputs such as "gazing" in weekday morning time zones.

(2.3. Modification)

Figure 8:
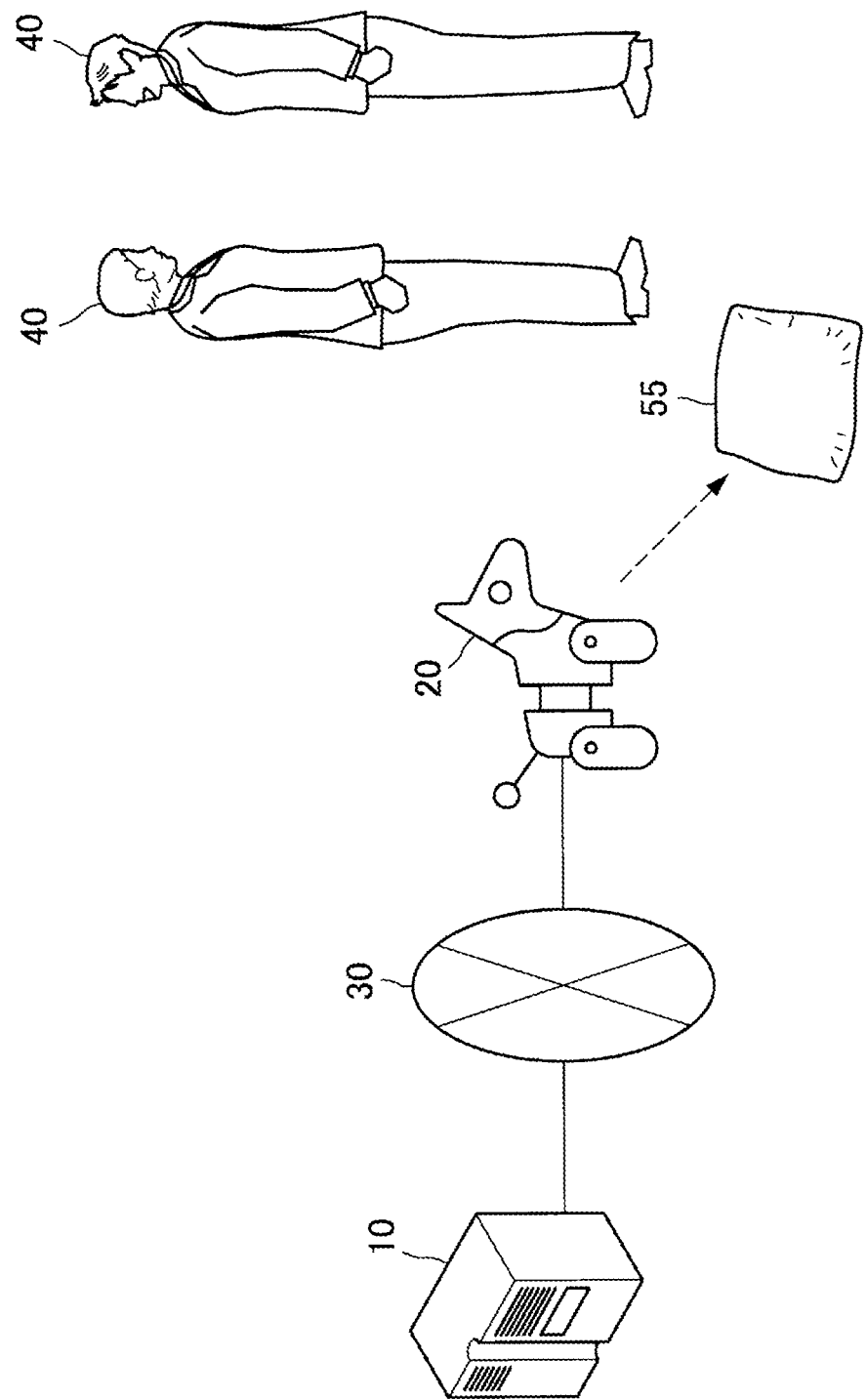
FIG. 8 is a diagram illustrating a modification of the system according to the embodiment.

Next, a modification of the system according to the present embodiment will be described with reference to FIG. 8. FIG. 8 is a diagram illustrating a modification of the system according to the present embodiment.

In the example described with reference to FIG. 7, the output of the robot device 20 is given based on an utterance regarding the robot device 20 of the user 40, as a trigger. However, the system according to the present embodiment is not limited to the above example. For example, the output of the robot device 20 may be given spontaneously.

Specifically, an example illustrated in FIG. 8 assumes a situation in which two users 40 are talking about a cushion 55 they have purchased. In such a case, since the two users 40 have not given an utterance related to the robot device 20, it is difficult for the information processing device 10 to determine an output that the two users 40 expect from the robot device 20 based on a message indicated in the utterance. Therefore, the information processing device 10 may bring out actions and emotions of the two users 40 by allowing the robot device 20 to spontaneously give an output to the two users 40.

For example, the information processing device 10 may control the robot device 20 to give an output to approach the cushion 55 as a topic of conversation of the two users 40. That is, the information processing device 10 may apply the output of the robot device 20 onto the object included in the utterances of the two users 40, thereby inducing an action or emotion from the users 40 toward the robot device 20. With this configuration, the information processing device 10 might be able to extract an utterance capable of estimating an emotion of "joy", such as "being happy to have bought a new cushion" from any of the users 40. In such a case, the information processing device 10 can accumulate interaction information in which an output of "approaching a new object" of the robot device 20, an action of performing "utterance regarding the new object" performed by the user 40, and an emotion of "joy" in the user 40 are associated with each other.

3. Second Embodiment 3.1. Configuration of Information Processing Device

Figure 9:
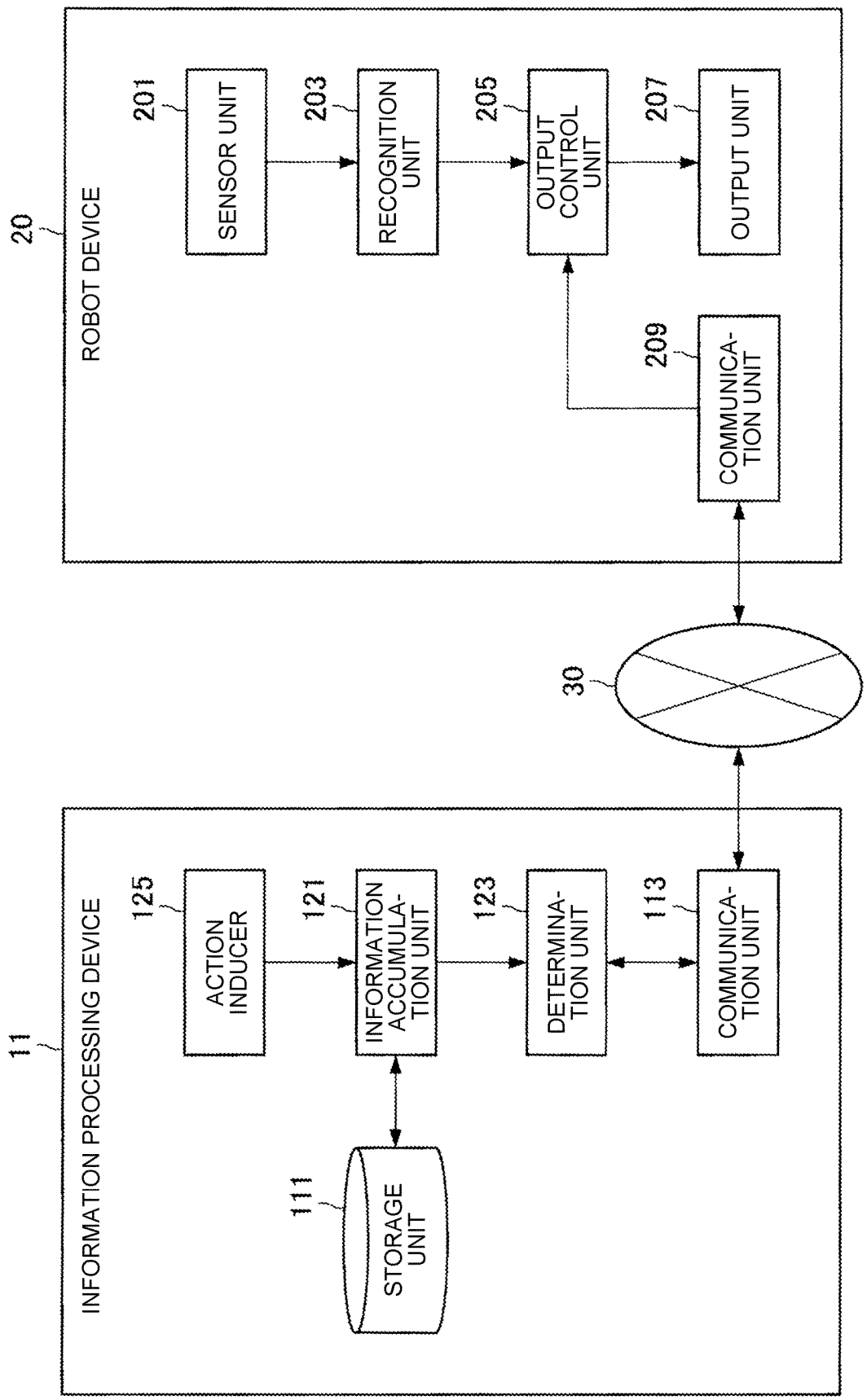
FIG. 9 is a block diagram illustrating a functional configuration of a system according to a second embodiment of the present disclosure.

Next, a second embodiment that implements the technology according to the present disclosure will be described with reference to FIG. 9. FIG. 9 is a block diagram illustrating a functional configuration of a system according to the second embodiment.

As illustrated in FIG. 9, the system according to the present embodiment includes an information processing device 11 and a robot device 20 connected to each other via a network 30.

The system according to the present embodiment controls the output of the robot device 20 based on the interaction information in the description of the system according to the first embodiment, thereby inducing a desired action or emotion in the user 40. For example, when it is desired to induce the user 40 to have a positive emotion toward an object, the system according to the present embodiment gives an output of the robot device 20 associated with the positive emotion of the user 40 in the interaction information so as to be associated with the object. With this control, it is considered that the user 40 will also have a positive emotion induced in correspondence with the output of the robot device 20, toward the object.

(Information Processing Device 11)

The information processing device 11 includes an action inducer 125, an information accumulation unit 121, a storage unit 111, a determination unit 123, and a communication unit 113.

The action inducer 125 determines an action or emotion to be induced in the user 40. Specifically, the action inducer 125 may determine to induce a positive emotion in the user 40 for a commercial regarding an object or induce a negative emotion in the user 40 in order to keep the user 40 away from the object. Alternatively, the action inducer 125 may determine to induce the user 40 to perform an action necessary for physical protection of the user 40 for safety. Furthermore, the action inducer 125 may determine to induce the user 40 to follow the robot device 20 in order to guide the action of the user 40. The action or emotion to be induced by the action inducer 125 in the user 40 may be appropriately selected according to the purpose. The action or emotion to be induced by the user 40 may be autonomously determined by the information processing device 11, or may be determined based on an instruction from the outside.

The information accumulation unit 121 accumulates the interaction information in the description of the system according to the first embodiment. That is, the information accumulation unit 121 accumulates the interaction information in which the output of the robot device 20, the action of the user 40 performed in correspondence with the output of the robot device 20, and the emotion of the user 40 estimated from the action of the user 40 are associated with each other. By using the accumulated interaction information, the information processing device 11 can determine an output of the robot device 20 that induces a desired action or emotion in the user 40. The interaction information accumulated in the information accumulation unit 121 may be generated and accumulated in the system according to the first embodiment, or may be introduced from the outside.

The interaction information is accumulated in the storage unit 111 as a constructed database, for example. The storage unit 111 may be actualized by, for example, a magnetic storage device such as an HDD, a semiconductor storage device such as an SSD, an optical storage device, a magneto-optical storage device, or the like.

The determination unit 123 determines an output of the robot device 20 corresponding to the action or emotion to be induced in the user 40 based on the accumulated interaction information. Specifically, the determination unit 123 extracts an output of the robot device 20 associated with the action or emotion to be induced in the user 40 from among pieces of the accumulated interaction information, and selects an output that can be executed by the robot device 20 from the extracted output of the robot device 20.

The output of the robot device 20 works as a stimulus on at least one or more of visual, auditory, or tactile senses of the user 40. The output of the robot device 20 that works as a stimulus on the visual sense may be, for example, presentation of an action of the robot device 20 to the user 40, or presentation of a video or an image from the robot device 20 to the user 40. The output of the robot device 20 that works as a stimulus on the auditory sense may be, for example, a sound output such as cries from the robot device 20. The output of the robot device 20 that works as a stimulus on the tactile sense may be, for example, presentation of vibration or thermal sensation by contact between the robot device 20 and the user 40, or presentation of non-contact tactile sense using an air gun.

The determination unit 123 may determine the details of the output of the robot device 20 according to the details and importance of the action or emotion induced by the user 40. For example, there is a case where the accumulated interaction information includes a plurality of outputs of the robot device 20 corresponding to the action or emotion to be induced in the user 40. In such a case, the determination unit 123 may select an appropriate output from among a plurality of outputs of the corresponding robot device 20 based on the details of the action or emotion to be induced in the user 40. For example, the determination unit 123 may determine to allow the robot device 20 to output more together with an increase in the importance of the action or emotion to be induced in the user 40.

For example, when immediately inducing an action or emotion in the user 40, presenting information after movement of the robot device 20 would cancel the immediacy of the information presentation. Therefore, in such a case, the determination unit 123 may first allow the robot device 20 to output sounds like cries to attract attention of the user 40 onto the robot device 20, and may thereafter determine to allow the robot device 20 to perform the movement and the information presentation. According to such control, the determination unit 123 can ensure the immediacy of information presentation.

Furthermore, the determination unit 123 may determine the details of the output of the robot device 20 based on the degree of interaction between the user 40 and the robot device 20 (that is, parameters such as frequency, duration, density, or depth of communication). For example, when the frequency of interaction between the user 40 and the robot device 20 is low, the determination unit 123 may determine to allow the robot device 20 to give a specific and more comprehensible output, such as voice or video.

For example, when inducing the user 40 to have a positive emotion toward a commercial for an object, the determination unit 123 may determine to allow the robot device 20 to give an output so as to associate the object with the output that induces the positive emotion in the user 40. Furthermore, when inducing the user 40 to have a negative emotion in order to keep the user 40 away from an object, the determination unit 123 may determine to allow the robot device 20 to give an output so as to associate the object with the output that induces the negative emotion in the user 40.

For example, when inducing the user 40 to perform an action necessary for physical protection of the user 40 for safety, the determination unit 123 may determine to allow the robot device 20 to give an output that would evoke an environmental physical influence on the user 40. With this configuration, it is possible, by the output of the robot device 20, to induce the user 40 to perform an action to avoid the environmental physical influence. Furthermore, when inducing the user 40 to perform an action necessary for physical protection of the user 40 for safety, the determination unit 123 may determine to allow the robot device 20 to give an output indicating that the robot device 20 has a problem due to the environment. With this configuration, the user 40 is induced to perform an action to solve the problem occurring in the robot device 20 through feeling of concern or care for the robot device 20.

For example, when inducing the user 40 to perform an action of following the robot device 20 in order to guide the action of the user 40, the determination unit 123 may determine to allow the robot device 20 to give an output to prompt the user 40 to perform a desired action. With this configuration, by giving the user 40 a sense of competition against the robot device 20, it is possible to guide the user 40 to follow the output of the robot device 20, enabling inducing the user 40 to perform a desired action.

Similarly to the first embodiment, the communication unit 113 is a communication interface for exchanging information between the information processing device 11 and the robot device 20. Since the communication unit 113 is substantially similar to the communication unit 113 described in the first embodiment, the description thereof will be omitted here.

(Robot Device 20)

The robot device 20 includes a sensor unit 201, a recognition unit 203, an output control unit 205, an output unit 207, and a communication unit 209. Since the function of each component of the robot device 20 is substantially similar to the function described in the first embodiment, the description thereof will be omitted here.

The functional groups constituting the system according to the present embodiment have been specifically described above. Similarly to the first embodiment, these function groups may be included in either the information processing device 11 or the robot device 20. Furthermore, these functional groups may be integrated in the robot device 20.

(3.2. Operation of Information Processing Device)

Next, operations of the system according to the present embodiment will be described with reference to FIGS. 10, 11A and 11B.

Figure 10:
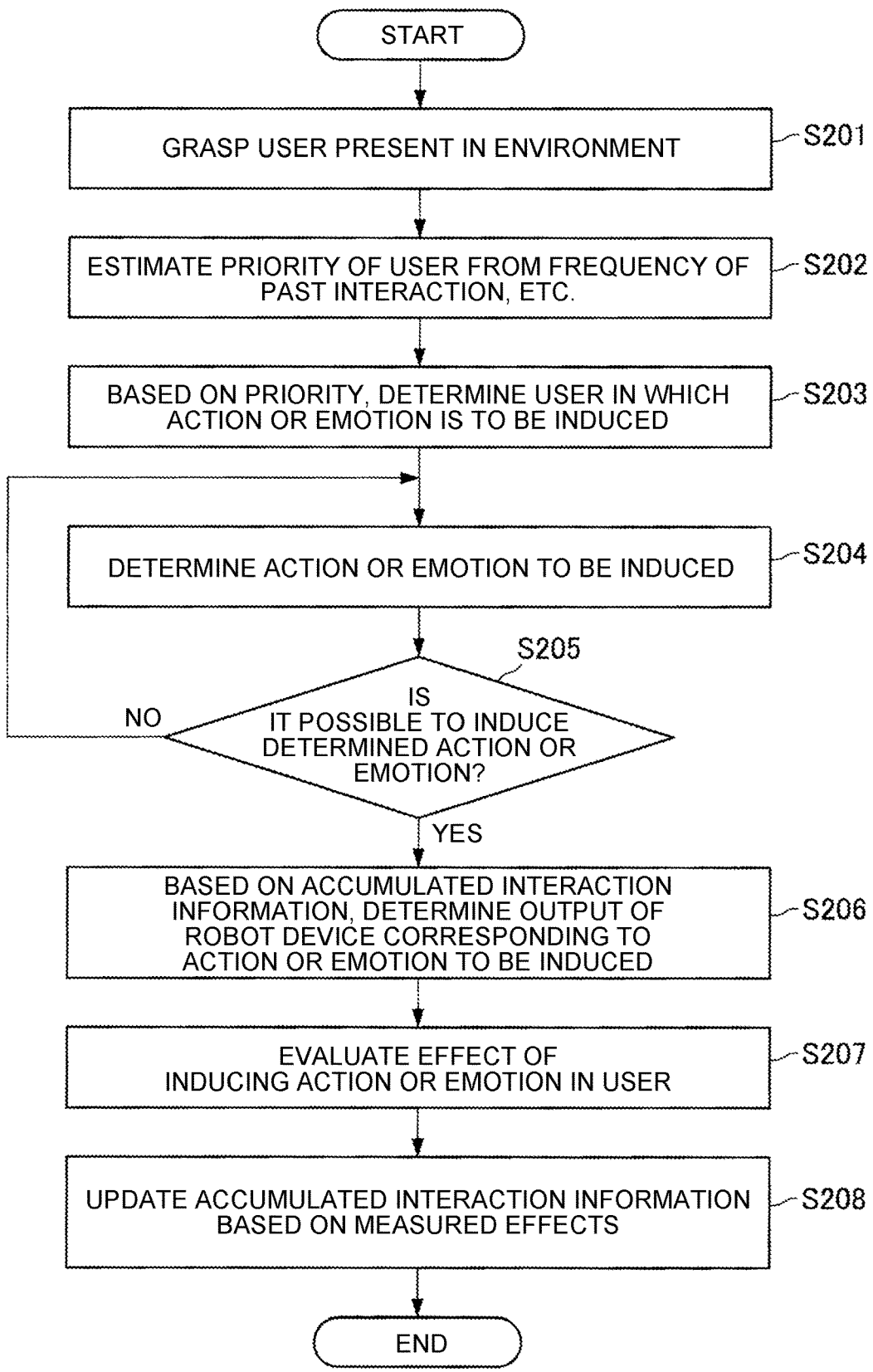
FIG. 10 is a flowchart illustrating an example of an operation executed by the system according to the embodiment.

FIG. 10 is a flowchart illustrating an example of an operation executed by the system according to the present embodiment. The operation example according to the flowchart illustrated in FIG. 10 is an operation example for the purpose of inducing a desired action or emotion in the user 40.

As illustrated in FIG. 10, first, the information processing device 11 grasps the user 40 existing in an environment based on a sensing result regarding the environment obtained by the sensor unit 101 (S201).

Subsequently, the information processing device 11 estimates the priority of the user 40 based on a history of past interactions between the user 40 and the robot device 20 (S202). For example, the information processing device 11 may estimate the priority of the user 40 based on parameters such as the frequency, duration, density, or depth of the interaction between the user 40 and the robot device 20. Alternatively, the information processing device 11 may estimate the priority of the user 40 based on the number of times of interaction from the user 40 to the robot device 20, or an operation history of the robot device 20 by the user 40 such as the number of times the user 40 has turned off the power of the robot device 20.

Next, based on the priority, the information processing device 11 determines the user 40 in which an action or emotion is to be induced (S203). The interaction information associates the outputs of the robot device 20 with the actions and emotions of the user 40 for each of users. Therefore, through the operations from step S201 to step S203, the information processing device 11 determines the user on whom reference to the interaction information is to be performed.

Note that the operation of determining the user 40 in steps S201 to S203 may be similar to the operation of the system according to the first embodiment described with reference to FIG. 7 (steps S101 to S102).

Thereafter, the information processing device 11 determines the action or emotion to be induced in the determined user 40 (S204). Specifically, the information processing device 11 determines an action or emotion to be induced in the user 40 based on an instruction from the outside or internal information processing. For example, the information processing device 11 may determine an action or emotion to be induced in the user 40 based on a purpose such as a commercial for appealing to the user 40 for an object, a health alert to the user 40 such as staying hydrated, or an accident prevention alert such as indicating a dangerous place.

Next, the information processing device 11 determines the possibility of execution of inducing an action or emotion in the user 40 (S205). For example, when inducing a positive emotion toward an object in the user 40 for the purpose of a commercial to appeal an object to the user 40, the information processing device 11 would have difficulty in inducing the emotion toward the object in the user 40 when an actual object, an advertisement, or the like of the object does not exist in the environment. The information processing device 11 determines the possibility of inducing an action or emotion in the user 40, thereby enabling the robot device 20 to induce the action or emotion in the user 40 at an appropriate timing.

When inducement of an action or emotion in the user 40 is executable (S205/Yes), the information processing device 11 determines an output of the robot device 20 corresponding to the action or emotion to be induced, based on the accumulated interaction information (S206). Specifically, the information processing device 11 extracts an output that has successfully induced the action or emotion in the user 40 from the accumulated interaction information, and allows the robot device 20 to appropriately output the extracted output.

In contrast, when inducement of the action or emotion in the user 40 is not executable (S205/No), the information processing device 11 returns to step S204 and re-determines the action or emotion to be induced in the user 40.

After the output is given from the robot device 20 to the user 40, the information processing device 11 evaluates the action or emotion of the user 40 in response to the output of the robot device 20, thereby measuring the effect of inducing the action or emotion (S207). Furthermore, the information processing device 11 may update the output of the robot device 20 in the interaction information so that the action or emotion in the user 40 is further induced based on the evaluation result of the action or emotion of the user 40 in response to the output of the robot device 20 (S208). Alternatively, the information processing device 11 may add, to the interaction information, information related to the degree of inducement of an action or emotion in the user 40 in response to the output of the robot device 20. With this configuration, the information processing device 11 can optimize the output of the robot device 20 for the user 40 so as to be able to induce a desired action or emotion through interaction between the user 40 and the robot device 20.

Figure 11A:
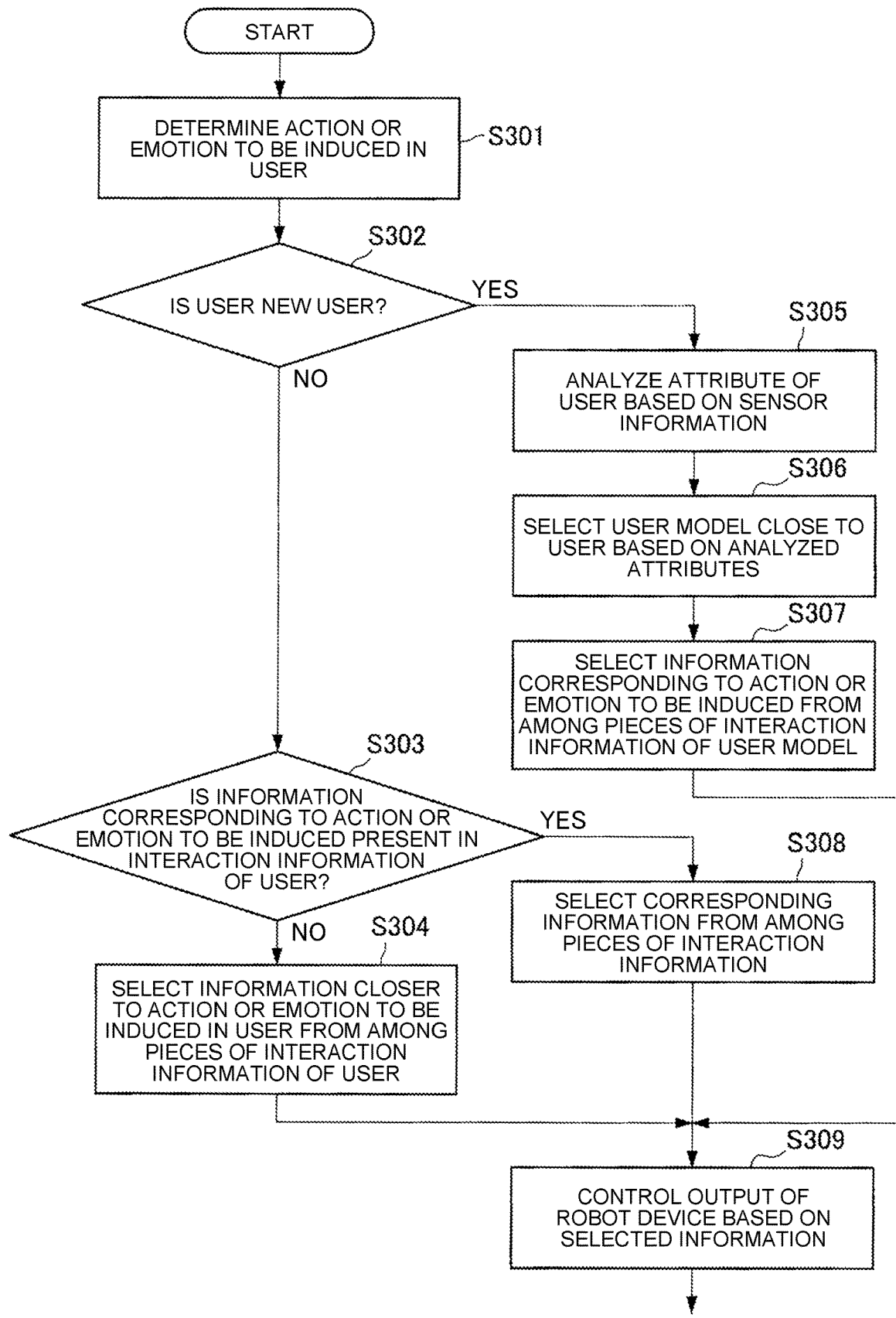
FIG. 11A is a flowchart illustrating another example of the operation executed by the system according to the embodiment.
Figure 11B:
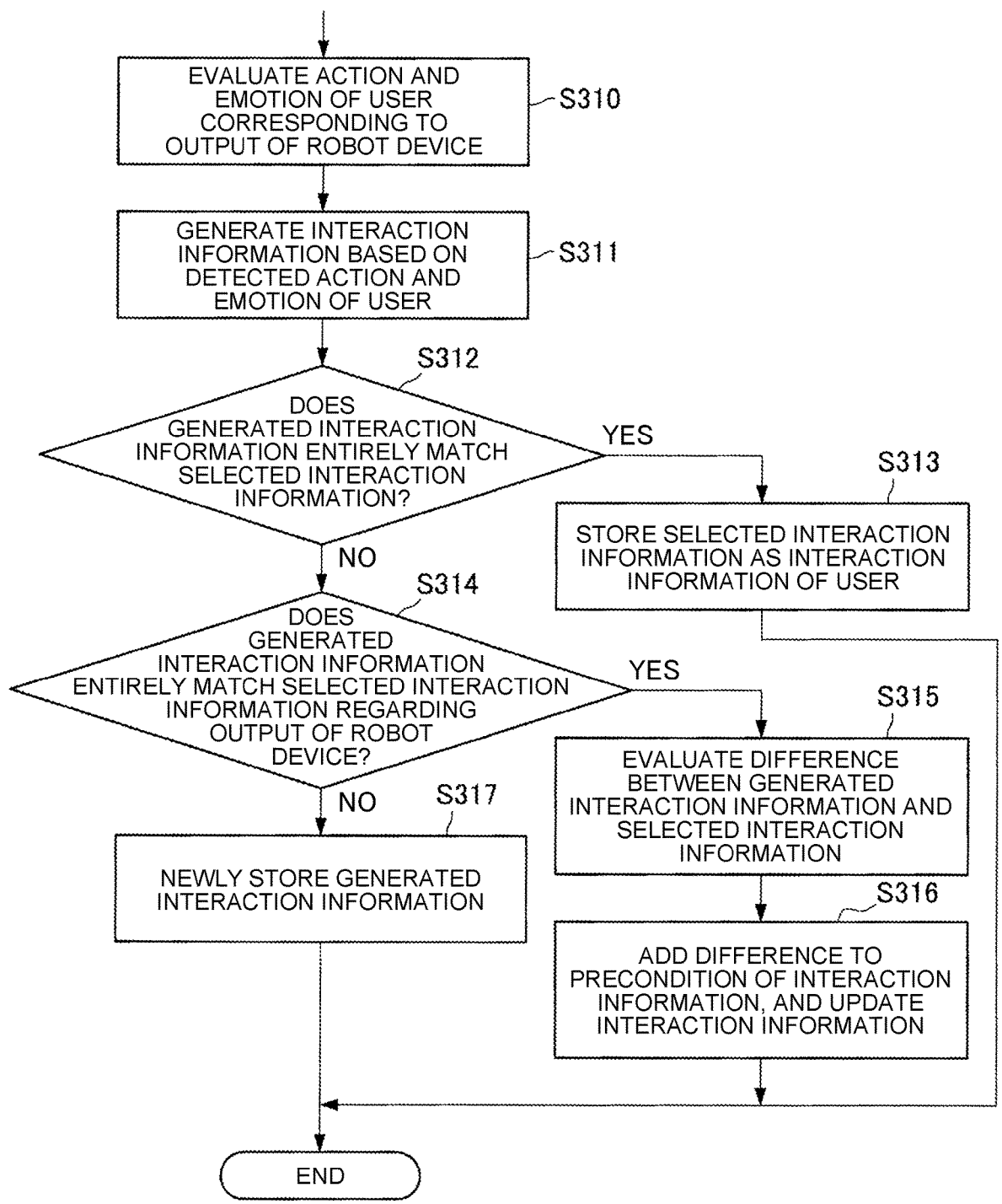
FIG. 11B is a flowchart illustrating another example of the operation executed by the system according to the embodiment.

FIGS. 11A and 11B are flowcharts illustrating another example of the operation executed by the system according to the present embodiment. The operation example illustrated in the flowcharts illustrated in FIGS. 11A and 11B is an operation example focusing on the operation related to the update of the interaction information by the information processing device 11 in the operation example described with reference to FIG. 10.

As illustrated in FIG. 11A, the information processing device 11 first determines an action or emotion to be induced in the user 40 (S301). Subsequently, the information processing device 11 determines whether or not the user 40 is a new user (S302).

When the user 40 is a new user (S302/Yes), the interaction information of the user 40 has not been accumulated in the information processing device 11. Therefore, the information processing device 11 analyzes attributes such as the age group and gender of the user 40 based on sensing information regarding the user 40 (S305), and selects a user model close to the user 40 based on the analyzed attributes (S306). The user model has preliminary settings of interaction information in which outputs of the robot device 20 are associated with actions and emotions of a typical user 40 in accordance with attributes such as age group and gender. By using the interaction information that has been set in the user model as provisional interaction information, the information processing device 11 can induce an action or emotion even in a new user having no accumulated interaction information. Thereafter, the information processing device 11 selects information corresponding to the action or emotion to be induced from among pieces of the interaction information of the selected user model (S307).

In contrast, when the user 40 is not a new user (S302/No), the interaction information of the user 40 has been accumulated in the information processing device 11. Therefore, the information processing device 11 determines whether or not interaction information corresponding to an action or an emotion to be induced is present in the interaction information of the user 40 (S303). When pieces of interaction information corresponding to an action or emotion to be induced are present (S303/Yes), the information processing device 11 selects corresponding information from among pieces of the interaction information (S308). When there is no interaction information corresponding to the induced action or emotion (S303/No), the information processing device 11 selects information corresponding to an action or emotion close to the action or emotion to be induced (S304).

Subsequently, the information processing device 11 controls the output of the robot device 20 based on the information selected in steps S304, S307, and S308 (S309). With this control, an output that induces a desired action or emotion is given from the robot device 20 to the user 40.

Thereafter, as illustrated in FIG. 11B, the information processing device 11 senses the action of the user 40 corresponding to the output of the robot device 20 (S310), and then estimates the emotion of the user 40 from the sensed action. Next, the information processing device 11 generates interaction information in which the output of the robot device 20 is associated with the action and emotion of the corresponding user 40, based on the evaluated action and emotion of the user 40 (S311).

Here, the information processing device 11 determines whether or not the interaction information selected at determination of the output of the robot device 20 entirely matches the generated interaction information (S312). When the selected interaction information entirely matches the generated interaction information (S312/Yes), the information processing device 11 stores the selected interaction information as the interaction information of the user 40 again (S313).

In contrast, when the selected interaction information does not entirely match the generated interaction information (S312/No), the information processing device 11 determines whether or not the selected interaction information and the generated interaction information achieve matching regarding the output of the robot device 20 (S314). When there is no matching regarding the outputs of the robot devices 20, (S314/No), the information processing device 11 newly stores the generated interaction information as new interaction information (S317).

When there is matching regarding the outputs of the robot devices 20 (S314/Yes), the information processing device 11 determines that the action or emotion of the user 40 has changed because the selected interaction information and the generated interaction information have different preconditions. Therefore, the information processing device 11 evaluates a difference between the selected interaction information and the generated interaction information (S315). Thereafter, the information processing device 11 adds the evaluated difference as a precondition, and individually stores the selected interaction information and the generated interaction information (S316).

Operations of steps S315 and S316 of the information processing device 11 will be described more specifically with reference to FIGS. 12 and 13. FIG. 12 is a table illustrating an example of generated interaction information and selected interaction information. FIG. 13 is a table illustrating an example of interaction information stored based on the example illustrated in FIG. 12.

As illustrated in FIG. 12, here is an assumable case, for example, where the interaction information selected to determine the output of the robot device 20 associates the action "touching the robot device" of the user 40 and the emotion "joy" in the user 40 with the output "approaching" of the robot device 20. In contrast, there can be another case where the interaction information generated by evaluating the action and emotion of the user 40 in response to the output of the robot device 20 associates the action of the user 40 "brushing off the robot device" and the emotion "anger" of the user 40 with the output "approaching" of the robot device 20.

In such a case, the information processing device 11 evaluates a difference between individual pieces of interaction information by referring to a status in which the individual pieces of interaction information are generated. For example, there can be a case where the selected interaction information is generated under the surrounding environment status that "user A is in neighborhood" in the time zone of "morning", while the generated interaction information is generated under the surrounding environment status that "user B is in neighborhood" in the time zone of "morning". At this time, the information processing device 11 can find a difference in a surrounding environment such as "user A is in neighborhood" or "user B is in neighborhood" as a difference in a status in which the two pieces of interaction information are generated.

Therefore, the information processing device 11 can add the information of the surrounding environment found as the difference between the two pieces of interaction information to each of the two pieces of interaction information as a precondition. Consequently, as illustrated in FIG. 13, the information processing device 11 can generate, from the selected interaction information, first interaction information to which the precondition of "the user A is in neighborhood" has been added, and can store the generated first interaction information. Furthermore, the information processing device 11 can generate, from the generated interaction information, second interaction information to which a precondition that "the user B is in neighborhood" has been added, and can store the generated second interaction information.

3.3. Application Examples

Next, specific application examples of the system according to the present embodiment will be described.

First Application Example

The system according to the present embodiment can be used in a commercial for a product to the user 40, for example.

For example, when it is desired to induce the user 40 to have an interest in a product, the information processing device 11 can control the output of the robot device 20 to give an output such as "bark to TV when commercial video of a certain product is displayed on TV" or "bring a product in the environment to the feet of the user 40". With this, the system according to the present embodiment can attract the user 40 to focus on the product.

Second Application Example

The system according to the present embodiment can be used for alerting for physical protection of the user 40, for example.

For example, when there is an obstacle in the environment against which the user 40 can hit his/her foot, or when the ambient temperature is high which can cause heatstroke in the user 40, the information processing device 11 can control the output of the robot device 20 to give an output of an action reminding the user 40 of a possible consequence.

Specifically, the information processing device 11 can induce the user 40 to perform an action of removing an obstacle by controlling the robot device 20 to output a behavior of being blocked by the obstacle or a behavior of being out of order due to the obstacle. Furthermore, the information processing device 11 can induce the user 40 to take a behavior for avoiding the heatstroke by controlling the robot device 20 to output some behavior such as a behavior indicating inability to move due to heatstroke, a behavior of drinking water, a behavior prompting the user to purchase a beverage, a behavior activating a cooling device such as air conditioner, or a behavior guiding the user to a cool place.

Third Application Example

Figure 14:
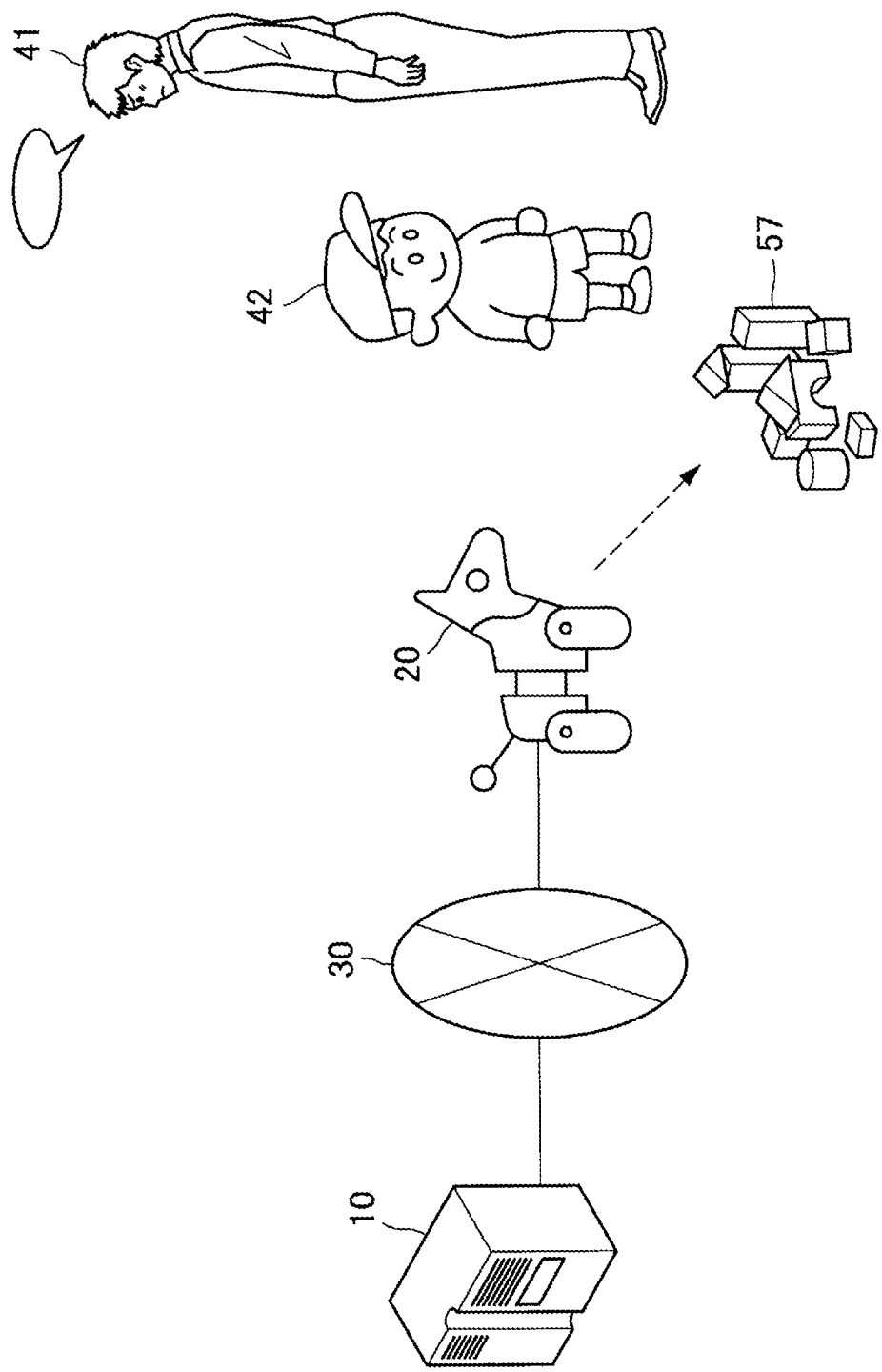
FIG. 14 is a diagram illustrating a third application example of the system according to the embodiment.

The system according to the present embodiment can be used to prompt the user 40 to follow an action of the robot device 20. A third use example will be described with reference to FIG. 14. FIG. 14 is a diagram illustrating a third application example of the system according to the present embodiment.

As illustrated in FIG. 14, here is an assumable case having a parent 41 and a child 42 as users of the system according to the present embodiment. The system according to the present embodiment can control the robot device 20 to execute an action desired, by the parent 41, to be performed by the child 42, by utilizing the sense of competition in the child 42 against the robot device 20, making it possible to induce the child 42 to follow the output of the robot device 20. That is, when a plurality of users 40 having a predetermined relationship are present, the system according to the present embodiment is also capable of inducing an action or emotion to a user other than the user 40 for whom interaction information has been accumulated, by considering the relationship between the users 40.

For example, the information processing device 11 may grasp an instruction from the parent 41 to the child 42 based on an utterance message of the parent 41, and may control the robot device 20 to give an output following the instruction from the parent 41 to the child 42.

Specifically, when having recognized the utterance message of the parent 41 such as "clean up the toy 57", the information processing device 11 can control the robot device 20 to give an output of cleaning up the toy 57 more proactively than the child 42. With this control, the robot device 20 can guide the child 42 to perform an action of cleaning up the toy 57 by stimulating the sense of competition in the child 42. Furthermore, when having recognized the utterance message of the parent 41 such as "come here", the information processing device 11 can control the robot device 20 to give an output of approaching the parent 41 more proactively than the child 42. With this control, the robot device 20 can guide the child 42 to perform an action following the utterance of the parent 41.

Note that the information processing device 11 may control the output of the robot device 20 based on a trigger other than the utterance of the parent 41. For example, in the presence of interaction information indicating that an emotion of joy in the parent 41 is induced by an output of cleaning up the toy 57 given by the robot device 20, the information processing device 11 may control the robot device 20 to give an output of cleaning up the toy 57 with detection of a state in which the toy 57 is not cleaned up, as a trigger. With this control, the robot device 20 can guide the child 42 to perform an action of cleaning up the toy 57 following the robot device 20.

4. Hardware Configuration

Furthermore, an example of a hardware configuration of the information processing device 10 constituting the system according to the first embodiment of the present disclosure will be described with reference to FIG. 15. FIG. 15 is a block diagram illustrating an example of a hardware configuration in the information processing device 10 constituting the system according to the first embodiment. Note that the hardware configuration of the information processing device 11 according to the second embodiment is substantially similar to the hardware configuration of the information processing device 10 according to the first embodiment, and thus the description thereof will be omitted here.

As illustrated in FIG. 15, the information processing device 10 includes a CPU 901, ROM 902, RAM 903, a host bus 905, a bridge 907, an external bus 906, an interface 908, an input device 911, an output device 912, a storage device 913, a drive 914, a connection port 915, and a communication device 916. The information processing device 10 may include a processing circuit such as an electric circuit, a digital signal processor (DSP), or an application specific integrated circuit (ASIC) instead of the CPU 901 or together with the CPU 901.

The CPU 901 functions as an arithmetic processing device or a control device, and controls the overall operation in the information processing device 10 according to various programs. In addition, the CPU 901 may be a microprocessor. The ROM 902 stores programs and calculation parameters used by the CPU 901. The RAM 903 temporarily stores a program used in the execution of the CPU 901, parameters that change appropriately in the execution, or the like. The CPU 901 may execute, for example, the functions of the recognition unit 103, the action evaluation unit 105, the emotion estimation unit 107, the information accumulation units 109 and 121, the determination unit 123, the action inducer 125, and the output control unit 205.

The CPU 901, ROM 902, and RAM 903 are connected to each other by the host bus 905 including a CPU bus or the like. The host bus 905 is connected to the external bus 906 such as a Peripheral Component Interconnect/Interface (PCI) bus via the bridge 907. Note that the host bus 905, the bridge 907, and the external bus 906 are not necessarily separated, and these functions may be mounted on one bus.

The input device 911 is a device used to input information by the user, and examples of which include a mouse, a keyboard, a touch panel, a button, a microphone, a switch, or a lever. Furthermore, the input device 911 may include, for example, an input control circuit that generates an input signal based on the information input by the user using the above described input means.

The output device 912 is a device capable of visually or audibly notifying the user of information. The output device 912 may be, for example, a display device such as a cathode ray tube (CRT) display device, a liquid crystal display device, a plasma display device, an electroluminescence (EL) display device, a laser projector, a light emitting diode (LED) projector, or a lamp, or may be a sound output device such as a speaker and a headphone.

The output device 912 may output, for example, results obtained by various types of processes performed by the information processing device 10. Specifically, the output device 912 may visually display the results obtained by various processes performed by the information processing device 10 in various formats such as texts, images, tables, and graphs. Alternatively, the output device 912 may convert an audio signal of audio data, acoustic data, or the like, into an analog signal and output the signal audibly.

The storage device 913 is a data storage device formed as an example of a storage unit of the information processing device 10. The storage device 913 may be actualized by, for example, a magnetic storage device such as a hard disk drive (HDD), a semiconductor storage device, an optical storage device, a magneto-optical storage device, or the like. The storage device 913 may include a storage medium, a recording device that records data on the storage medium, a reading device that reads data from the storage medium, a deleting device that deletes the data recorded on the storage medium, or the like. The storage device 913 may store programs to be executed by the CPU 901, various data, as well as various data acquired from the outside, or the like. The storage device 913 may execute the function of the storage unit 111, for example.

The drive 914 is a reader/writer for a storage medium, and is built in or externally connected to the information processing device 10. The drive 914 reads information recorded on a removable storage medium such as a mounted magnetic disc, optical disc, magneto-optical disc, or semiconductor memory, and outputs the read information to the RAM 903. The drive 914 is also capable of writing information to the removable storage medium.

The connection port 915 is an interface connected to an external device. For example, the connection port 915 may be a connection port capable of performing data exchange with an external device, and may be a Universal Serial Bus (USB), for example.

The communication device 916 is, for example, an interface formed by a communication device or the like for connecting to a network 30. The communication device 916 may be, for example, a communication card for wired or wireless Local Area Network (LAN), Long Term Evolution (LTE), Bluetooth (registered trademark), Wireless USB (WUSB), or the like. Furthermore, the communication device 916 may be an optical communication router, an Asymmetric Digital Subscriber Line (ADSL) router, a modem for various communications, or the like. The communication device 916 can exchange signals or the like over the Internet and with other communication devices in accordance with a predetermined protocol such as TCP/IP.

The connection port 915 or the communication device 916 may execute the functionalities of the communication unit 113.

Incidentally, it is also possible to create a computer program for allowing hardware devices such as a CPU, ROM, and RAM built in the information processing device 10 to exert the functions equivalent to the individual configurations of the information processing device 10 constituting the system according to the present embodiment described above. A storage medium storing the computer program can also be provided.

The preferred embodiments of the present disclosure have been described in detail above with reference to the accompanying drawings. However, the technical scope of the present disclosure is not limited to such examples. It will be apparent to those skilled in the art of the present disclosure that various modifications and alterations can be conceived within the scope of the technical idea described in the claims and naturally fall within the technical scope of the present disclosure.

Furthermore, the effects described in the present specification are merely illustrative or exemplary and are not limited. That is, the technique according to the present disclosure can exhibit other effects that are apparent to those skilled in the art from the description of the present specification in addition to or instead of the above effects.

Note that the following configurations also belong to the technical scope of the present disclosure.

(1)

An information processing device comprising:
    an output control unit that controls an output from an interaction device to a user;
    an action evaluation unit that determines an action of the user performed in correspondence with an output of the interaction device;
    an emotion estimation unit that estimates an emotion of the user corresponding to the action of the user; and
    an information accumulation unit that accumulates the output of the interaction device, the action of the user, and the emotion of the user in association with each other as interaction information,
    wherein the output control unit controls the output from the interaction device to the user based on the interaction information accumulated.

(2)

The information processing device according to (1), wherein the action evaluation unit determines the action of the user performed in correspondence with the output from the interaction device by listing the output of the interaction device and the action of the user in a same time series.

(3)

The information processing device according to (2), wherein, when the output of the interaction device and the action of the user have been continuously performed within a predetermined time, the action evaluation unit determines that the output of the interaction device corresponds to the action of the user.

(4)

The information processing device according to (2) or (3), wherein, when the action of the user has been changed after the output performed by the interaction device, the action evaluation unit determines that the output performed by the interaction device corresponds to the changed action of the user.

(5)

The information processing device according to any one of (1) to (4), wherein the emotion estimation unit estimates the emotion of the user corresponding to the action of the user by comparing speech and action set to be related to each of types of emotions with the action of the user.

(6)

The information processing device according to any one of (1) to (5), wherein the interaction information further includes information related to a precondition that associates the output of the interaction device, the action of the user, and the emotion of the user with each other.

(7)

The information processing device according to (6), wherein, when the action or the emotion of the user corresponding to the same output of the interaction device varies in a plurality of pieces of the interaction information, a difference in a surrounding environment of the interaction device or the user is added to each of the plurality of pieces of the interaction information, as the precondition.

(8)

The information processing device according to any one of (1) to (7), wherein, when the user exists in plurality, the output control unit determines a user to which the interaction device is to give an output, based on priority set for each of the users.

(9)

The information processing device according to (8), wherein the priority is set based on at least any one or more of frequency, time, and depth of interaction regarding the interaction device with each of the users.

(10)

The information processing device according to any one of (1) to (9), wherein the output control unit estimates an output expected by the user to be given from the interaction device based on content of an utterance of the user, and controls the interaction device to give the estimated output.

(11)

The information processing device according to (10), wherein the output control unit controls the interaction device to give an output executable by the interaction device among outputs of a plurality of patterns expected by the user to be given from the interaction device.

(12)

The information processing device according to (11), wherein the output control unit provides a waiting time of a predetermined length from a point of the utterance of the user until a point of output given by the interaction device to the user.

(13)

The information processing device according to (12), wherein the output control unit randomly controls the length of the waiting time for each of output performed by the interaction device.

(14)

The information processing device according to any one of (1) to (13), wherein the interaction device is a robot device.

(15)

The information processing device according to any one of (1) to (14), wherein the interaction device gives an output that works as a stimulus on at least one or more of visual, auditory, and tactile senses of the user.

(16)

An information processing method to be executed by an arithmetic processing device, the information processing method comprising:
controlling an output from an interaction device to a user;
determining an action of the user performed in correspondence with an output of the interaction device;
estimating an emotion of the user corresponding to the action of the user; and
accumulating the output of the interaction device, the action of the user, and the emotion of the user in association with each other as interaction information, and
controlling the output from the interaction device to the user based on the interaction information accumulated.

(17)

A program causing a computer to function as units comprising:
an output control unit that controls an output from an interaction device to a user;
an action evaluation unit that determines an action of the user performed in correspondence with an output of the interaction device;
an emotion estimation unit that estimates an emotion of the user corresponding to the action of the user; and
an information accumulation unit that accumulates the output of the interaction device, the action of the user, and the emotion of the user in association with each other as interaction information, and
the program further causing the output control unit to function so as to control the output from the interaction device to the user based on the interaction information accumulated.

REFERENCE SIGNS LIST 10, 11 INFORMATION PROCESSING DEVICE
20 ROBOT DEVICE
30 NETWORK
40 USER
101 SENSOR UNIT
103 RECOGNITION UNIT
105 ACTION EVALUATION UNIT
107 EMOTION ESTIMATION UNIT
109 INFORMATION ACCUMULATION UNIT
111 STORAGE UNIT
113 COMMUNICATION UNIT
121 INFORMATION ACCUMULATION UNIT
123 DETERMINATION UNIT
125 ACTION INDUCER
201 SENSOR UNIT
203 RECOGNITION UNIT
205 OUTPUT CONTROL UNIT
207 OUTPUT UNIT
209 COMMUNICATION UNIT

The invention claimed is:

1. An information processing device, comprising:
a plurality of sensors configured to determine biological information of a first user, wherein the biological information comprises a heart rate of the first user, a blood pressure of the first user, and a body temperature of the first user; and
a central processing unit (CPU) configured to:
determine an action of the first user, wherein the action is in correspondence with an output of an interaction device;
determine an emotion of the first user based on the biological information, wherein the emotion of the first user corresponds to the action of the first user;
determine interaction information based on the output of the interaction device, the action of the first user, and the emotion of the first user; and
control transmission of the output from the interaction device to the first user based on the interaction information.

2. The information processing device according to claim 1, wherein the CPU is further configured to:
list the output of the interaction device and the action of the first user in a same time series; and
determine the action of the first user based on the list.

3. The information processing device according to claim 2, wherein the CPU is further configured to determine the output of the interaction device based on
the action of the first user, and
the output of the interaction device and the action of the first user in a specific time.

4. The information processing device according to claim 2, wherein the CPU is further configured to determine the output of the interaction device based on a change in the action of the first user.

5. The information processing device according to claim 1, wherein the CPU is further configured to:
compare speech of the first user and an action set of the first user with the determined action of the first user; and
determine the emotion of the first user based on the action of the first user and the comparison of the speech of the first user and the action set of the first user with the determined action of the first user, and
the action set is associated with a plurality of types of emotions of the first user.

6. The information processing device according to claim 1, wherein
the interaction information further includes information related to a specific condition, and
the specific condition is associated with the output of the interaction device, the action of the first user, and the emotion of the first user.

7. The information processing device according to claim 6, wherein the CPU is further configured to:
determine a difference in surrounding environment of the first user based on a plurality of pieces of the interaction information; and
add the determined difference to each of the plurality of pieces of the interaction information, and
the specific condition is associated with the plurality of pieces of the interaction information.

8. The information processing device according to claim 1, wherein the CPU is further configured to:
determine a priority for each of a plurality of users;
determine a second user of the plurality of users based on the determined priority; and
control the transmission of the output, from the interaction device to the determined second user, based on the determined priority for the each of the plurality of users.

9. The information processing device according to claim 8, wherein
the CPU is further configured to determine the priority based on at least one of frequency of interaction, a time of the interaction, or a depth of the interaction, and
the interaction is between the interaction device and the each of the plurality of users.

10. The information processing device according to claim 1, wherein the CPU is further configured to:
determine a specific output, from the interaction device, based on an utterance of the first user; and
control the transmission of the specific output from the interaction device to the first user.

11. The information processing device according to claim 10, wherein the CPU is further configured to:
determine a plurality of patterns associated with a plurality of outputs from the interaction device; and
control the transmission of an executable output of the plurality of outputs from the interaction device, based on the determined plurality of patterns.

12. The information processing device according to claim 11, wherein
the CPU is further configured to determine a waiting time of a specific length, and
the specific length of the waiting time extends from a first point of the utterance of the first user to a second point of the transmission of the determined output by the interaction device to the first user.

13. The information processing device according to claim 12, wherein the CPU is further configured to control the specific length of the waiting time for each of the plurality of outputs.

14. The information processing device according to claim 1, wherein the interaction device is a robot device.

15. The information processing device according to claim 1, wherein
the CPU is further configured to control transmission of a stimulus output from the interaction device, and
the stimulus output is configured a stimulus on at least one of a visual of the first user, an auditory of the first user, or tactile senses of the first user.

16. An information processing method comprising:
determining biological information of a user, wherein the biological information comprises a heart rate of the user, a blood pressure of the user, and a body temperature of the user;
determining an action of the user, wherein the action is in correspondence with an output of an interaction device;
determining an emotion of the user based on the biological information, wherein the emotion of the user corresponds to the action of the user;
determining interaction information based on the output of the interaction device, the action of the user, and the emotion of the user; and
controlling transmission of the output from the interaction device to the user based on the interaction information.

17. A non-transitory computer-readable medium having stored thereon, computer-executable instructions which, when executed by a processor, cause the processor to execute operations, the operations comprising:
determining biological information of a user, wherein the biological information comprises a heart rate of the user, a blood pressure of the user, and a body temperature of the user;
determining an action of the user, wherein the action is in correspondence with an output of an interaction device;
determining an emotion of the user based on the biological information, wherein the emotion of the user corresponds to the action of the user;
determining interaction information based on the output of the interaction device, the action of the user, and the emotion of the user; and
controlling transmission of the output from the interaction device to the user based on the interaction information.

* * * * *